(12) United States Patent
Sherlock et al.

(10) Patent No.: US 10,596,048 B2
(45) Date of Patent: Mar. 24, 2020

(54) METHODS AND SYSTEMS FOR FORMING MOISTURE ABSORBING PRODUCTS FROM A MICROCROP

(71) Applicant: PARABEL LTD., Grand Cayman (KY)

(72) Inventors: Peter Sherlock, Rockledge, FL (US); Marcus Kenny, Kincardinshire (GB)

(73) Assignee: Parabel Ltd., Melbourne, FL (US)

( * ) Notice: Subject to any disclaimer, the term of this patent is extended or adjusted under 35 U.S.C. 154(b) by 950 days.

(21) Appl. No.: 15/179,968

(22) Filed: Jun. 10, 2016

(65) Prior Publication Data

US 2016/0361211 A1    Dec. 15, 2016

Related U.S. Application Data

(60) Provisional application No. 62/173,645, filed on Jun. 10, 2015.

(51) Int. Cl.
| | | |
|---|---|---|
| *A61F 13/15* | (2006.01) | |
| *B01J 20/22* | (2006.01) | |
| *B01J 20/30* | (2006.01) | |
| *A61F 13/84* | (2006.01) | |
| *A01K 1/015* | (2006.01) | |
| *B01J 20/24* | (2006.01) | |
| *B01D 25/12* | (2006.01) | |
| *B01D 33/54* | (2006.01) | |
| *B04B 1/20* | (2006.01) | |

(52) U.S. Cl.
CPC ............ *A61F 13/84* (2013.01); *A01K 1/0152* (2013.01); *A01K 1/0155* (2013.01); *A61F 13/15617* (2013.01); *A61F 13/15707* (2013.01); *A61F 13/15723* (2013.01); *A61F 13/8405* (2013.01); *B01D 25/12* (2013.01); *B01D 33/54* (2013.01); *B01J 20/22* (2013.01); *B01J 20/24* (2013.01); *B01J 20/3007* (2013.01); *B01J 20/3085* (2013.01); *B01J 20/3092* (2013.01); *B04B 1/20* (2013.01); *A61F 2013/15715* (2013.01); *A61F 2013/8435* (2013.01); *B01J 2220/485* (2013.01)

(58) Field of Classification Search
CPC .............. A01K 1/0152; A01K 1/0155; A61F 13/15617; A61F 13/15707; A61F 13/15723; A61F 13/84; A61F 13/8405; A61F 2013/15715; A61F 2013/8435; B01D 25/12; B01D 33/54; B01J 20/22; B01J 20/24; B01J 20/3007; B01J 20/3085; B01J 20/3092; B01J 2220/485; B04B 1/20

See application file for complete search history.

(56) References Cited

U.S. PATENT DOCUMENTS

| | | |
|---|---|---|
| 2,522,513 A | 9/1950 | Hemmeter |
| 296,200 A | 10/1954 | Olson |
| 2,827,454 A | 3/1958 | Gustav |
| 2,867,945 A | 1/1959 | Gotaas et al. |
| 3,468,057 A | 9/1969 | Buisson et al. |
| 3,499,687 A | 3/1970 | Ellis |
| 3,674,501 A | 7/1972 | Betz et al. |
| 3,704,041 A | 11/1972 | Loveland et al. |
| 3,768,200 A | 10/1973 | Klock |
| 3,839,198 A | 10/1974 | Shelef |
| 3,930,450 A | 1/1976 | Symons |
| 3,955,318 A | 5/1976 | Hulls |
| 4,005,546 A | 2/1977 | Oswald |
| 4,041,640 A | 8/1977 | Itanami et al. |
| 4,066,633 A | 1/1978 | Gastineau et al. |
| 4,077,158 A | 3/1978 | England |
| 4,137,868 A | 2/1979 | Pryor |
| 4,253,271 A | 3/1981 | Raymond |
| 4,429,867 A | 2/1984 | Barber |
| 4,516,528 A | 3/1985 | Jones |
| 4,557,937 A | 12/1985 | Bournier |

(Continued)

FOREIGN PATENT DOCUMENTS

| | | |
|---|---|---|
| CN | 101116986 | 2/2008 |
| CN | 101595943 | 12/2009 |

(Continued)

OTHER PUBLICATIONS

International search report and written opinion of the international searching authority for co-pending PCT application No. PCT/US2016/037099 dated Oct. 5, 2016.

(Continued)

*Primary Examiner* — Aaron J Kosar
(74) *Attorney, Agent, or Firm* — Baker & McKenzie LLP

(57) ABSTRACT

The present disclosure relates, according to some embodiments, to methods and systems for deriving odor- and moisture-absorbing products from a microcrop (e.g., photosynthetic aquatic species). More specifically, the present disclosure relates, in some embodiments, to forming an absorptive product from *Lemna*, including an animal litter, an animal bedding, a diaper product, a spill clean-up product, and any combination thereof. A process for forming an absorbent product from a microcrop may comprise the actions of (a) lysing the microcrop to generate a lysed microcrop; (b) separating the lysed microcrop into a solid fraction and a juice fraction; (c) processing the solid fraction to generate an absorbent solid; and/or (d) forming, by a shaping unit, the absorbent solid into pellets or granules that may be incorporated into the absorptive product. An absorptive product may have odor-reducing properties that are due in part to chlorophyll (e.g., from a microcrop).

8 Claims, 12 Drawing Sheets

(2 of 12 Drawing Sheet(s) Filed in Color)

(56) References Cited

U.S. PATENT DOCUMENTS

| | | | |
|---|---|---|---|
| 4,560,032 | A | 12/1985 | Imanaka |
| 4,604,948 | A | 8/1986 | Goldhahn |
| 4,840,253 | A | 6/1989 | DiMaggio et al. |
| 4,910,912 | A | 3/1990 | Lowrey, III |
| 5,047,332 | A | 9/1991 | Chahal |
| 5,121,708 | A | 6/1992 | Nuttle |
| 5,171,592 | A | 12/1992 | Holtzapple et al. |
| 5,269,819 | A | 12/1993 | Porath |
| 5,527,456 | A | 6/1996 | Jensen |
| 5,659,977 | A | 8/1997 | Jensen et al. |
| 5,667,445 | A | 9/1997 | Lochtefeld |
| 5,704,733 | A | 1/1998 | de Greef |
| 5,941,165 | A | 8/1999 | Butte |
| 6,077,548 | A | 6/2000 | Lasseur et al. |
| 6,096,546 | A | 8/2000 | Raskin |
| 6,251,643 | B1 | 6/2001 | Hansen et al. |
| 6,348,347 | B1 | 2/2002 | Hirabayashi et al. |
| 7,058,197 | B1 | 6/2006 | McGuire et al. |
| 7,215,420 | B2 | 5/2007 | Gellerman et al. |
| 7,674,077 | B2 | 3/2010 | Opatril |
| 8,245,440 | B2 | 8/2012 | Ryan et al. |
| 8,287,740 | B2 | 10/2012 | Newman et al. |
| 8,722,878 | B2 | 5/2014 | Raines et al. |
| 9,675,054 | B2 | 6/2017 | Grajcar et al. |
| 2004/0030516 | A1 | 2/2004 | Dunhill et al. |
| 2004/0144025 | A1 | 7/2004 | Johnson Rutzke |
| 2006/0024689 | A1 | 2/2006 | Bleuart et al. |
| 2007/0048859 | A1 | 3/2007 | Sears |
| 2007/0151522 | A1 | 7/2007 | Brauman |
| 2008/0032349 | A1 | 2/2008 | Visckov et al. |
| 2008/0096267 | A1 | 4/2008 | Howard et al. |
| 2008/0155890 | A1 | 7/2008 | Oyler |
| 2009/0088757 | A1 | 4/2009 | Tulkis |
| 2009/0151240 | A1 | 6/2009 | Kayama et al. |
| 2009/0285642 | A1 | 11/2009 | De Greef |
| 2010/0041095 | A1 | 2/2010 | Zeikus |
| 2010/0151558 | A1 | 6/2010 | Alianell et al. |
| 2010/0162620 | A1 | 7/2010 | McCaffrey et al. |
| 2010/0281836 | A1 | 11/2010 | Vanhoute et al. |
| 2010/0325948 | A1 | 12/2010 | Parsheh et al. |
| 2011/0016773 | A1 | 1/2011 | Nichols et al. |
| 2011/0092726 | A1 | 4/2011 | Clarke |
| 2011/0172102 | A1 | 7/2011 | Jacob et al. |
| 2012/0009660 | A1 | 1/2012 | Pottathil et al. |
| 2012/0171753 | A1 | 7/2012 | Ivry |
| 2012/0288917 | A1 | 11/2012 | Krenbrink |
| 2012/0308989 | A1 | 12/2012 | Barclay et al. |
| 2013/0023044 | A1 | 1/2013 | Gleason |
| 2013/0183705 | A1 | 7/2013 | Barclay et al. |
| 2013/0192130 | A1 | 8/2013 | Eckelberry |
| 2013/0244309 | A1 | 9/2013 | Singh et al. |
| 2014/0023675 | A1 | 1/2014 | Lina et al. |
| 2014/0212955 | A1 | 7/2014 | Ploechinger |
| 2014/0221630 | A1 | 8/2014 | Olivier et al. |
| 2014/0338261 | A1 | 11/2014 | Sykes |
| 2014/0356496 | A1 | 12/2014 | Melnyczuk |
| 2015/0072400 | A1 | 3/2015 | Clarke |
| 2015/0275161 | A1 | 10/2015 | Gressel et al. |
| 2016/0030350 | A1 | 2/2016 | Muller |
| 2016/0288001 | A1 | 10/2016 | Johnson |
| 2016/0360715 | A1 | 12/2016 | Sherlock et al. |
| 2017/0223935 | A1 | 8/2017 | Behrens |
| 2018/0014486 | A1 | 1/2018 | Creechley et al. |
| 2018/0118595 | A1 | 5/2018 | Curry |

FOREIGN PATENT DOCUMENTS

| | | | |
|---|---|---|---|
| CN | 102448286 | | 5/2012 |
| CN | 202960947 | | 6/2013 |
| CN | 204092345 | | 1/2015 |
| CN | 104413257 | | 3/2015 |
| DE | 4133920 | | 11/1993 |
| EP | 0285195 | | 10/1988 |
| EP | 0765599 | | 4/1997 |
| EP | 1543847 | A1 * | 6/2005 ............. A61L 15/46 |
| FR | 2522479 | | 9/1983 |
| GB | 1228039 | A * | 4/1971 ......... A61F 13/2051 |
| JP | S52151199 | | 12/1977 |
| JP | S54147650 | | 11/1979 |
| JP | S54147650 | A | 11/1979 |
| JP | 2004097021 | | 4/2004 |
| JP | 2005007837 | | 1/2005 |
| KR | 20000018164 | U | 10/2000 |
| KR | 101153379 | | 6/2012 |
| MX | 2011010995 | | 1/2012 |
| WO | 9105849 | | 5/1991 |
| WO | 9818344 | | 5/1998 |
| WO | 0145523 | | 6/2001 |
| WO | 2002034755 | | 5/2002 |
| WO | 03028432 | | 4/2003 |
| WO | 2007109066 | | 9/2007 |
| WO | 2008020457 | | 2/2008 |
| WO | 2008033573 | | 3/2008 |
| WO | 2010123943 | | 10/2010 |
| WO | 2010144877 | | 12/2010 |
| WO | 2011044194 | | 4/2011 |
| WO | 2011116252 | | 9/2011 |
| WO | 2011156662 | | 12/2011 |
| WO | 2014046543 | | 3/2014 |

OTHER PUBLICATIONS

Supplementary European Search Report in European Patent Application No. 16808482.0, dated Feb. 21, 2019.
First Examination Report in Australian Patent Application No. 2016276974, dated Apr. 9, 2019.
Office Action, mailed in Chinese Patent Application No. 201610789415.0 dated Apr. 26, 2019.
Examination Report, mailed in related Chinese Patent Application No. 201080023569.X, dated Sep. 20, 2012.
Office Action, mailed in Brazilian Patent Application No. PI1015000-5, notification published Jan. 23, 2018.
Office Action mailed in Brazilian Patent Application No. PI1015000-5, dated Dec. 20, 2017.
International Search Report and Written Opinion of the International Searching Authority (US) in related International Application No. PCT/US2010/031811, dated Jun. 18, 2010.
International Preliminary Report on Patentability of the International Preliminary Examination Authority (US) in related International Application No. PCT/US2010/031811, dated Oct. 11, 2011.
Office Action received in Brazilian Patent Application No. PI1015000-5, notification published May 10, 2018.
Office Action, mailed in Chinese Patent Application No. 201610789415.0 dated Nov. 5, 2018.
International Search Report and Written Opinion of the International Searching Authority (US) in PCT International Application No. PCT/US2011/028911, dated Nov. 30, 2011.
Office Action in Mexican Patent Application No. MX/A/2014/010053, dated Feb. 13, 2017.
Office Action mailed in Malaysian Patent Application No. PI 2011005000 dated Jun. 30, 2015.
Extended Search Report in European Patent Application No. 11757038.2, dated Mar. 9, 2017.
Office Action in European Patent Application No. 11757038.2, dated Jul. 16, 2018.
Office Action in Australian Patent Application No. 2015255285, dated Mar. 3, 2017.
Preliminary Examination Report in Peruvian Patent Application No. 1563-2012, dated Apr. 17, 2017.
International Preliminary Report on Patentability of the International Preliminary Examination Authority in PCT International Application No. PCT/US2011/028911, dated Sep. 18, 2012.
Office Action in Canadian Patent Application No. 2793512, dated Mar. 28. 2018.
Office Action in Canadian Patent Application No. 2793512, dated Aug. 7, 2017.
Office Action in Indonesian Patent Application No. W00201204170, dated Sep. 29, 2017.

(56) References Cited

OTHER PUBLICATIONS

Office Action in Japanese Patent Application No. 2015-020932 dated Jan. 27, 2017.
Office Action in Japanese Patent Application No. 2015-020932 dated Dec. 5, 2017.
Office Action in Indian Patent Application No. 8902/DELNP/2012 dated Aug. 3, 2018.
Office Action in European Patent Application No. 11757038.2, dated Jan. 3, 2019.
International Preliminary Report on Patentability by the International Preliminary Examination Authority for International Application No. PCT/US2016/037097, dated Dec. 22, 2017.
Cheng et al., "Growing Duckweed to Recover Nutrients from Wastewaters and for Production of Fuel Ethanol and Animal Feed", Clean, vol. 37, No. 1, pp. 17-26 (2009).
International Preliminary Report on Patentability by the International Preliminary Examination Authority (Korean Intellectual Patent Office) for International Application No. PCT/US2016/037099, dated Dec. 12, 2017.
Extended Search Report in European Patent Application No. 16808483.8, dated Dec. 21, 2018.
International Preliminary Report on Patentability by the International Preliminary Examination Authority (Korean Intellectual Patent Office) for International Application No. PCT/US2016/037046, dated Dec. 12, 2017.
International Preliminary Report on Patentability by the International Preliminary Examination Authority (Korean Intellectual Patent Office) for International Application No. PCT/US2016/041156, dated Jan. 18, 2018.
International Search Report and Written Opinion of the International Searching Authority (Korean Intellectual PatentOffice) for corresponding PCT application No. PCT/US2016/046422, dated Nov. 10, 2016.
International Preliminary Report on Patentability by the International Preliminary Examination Authority (Korean Intellectual Patent Office) for International Application No. PCT/US2016/046422, dated Feb. 22, 2018.
International Search Report and Written Opinion of the International Searching Authority for PCT application No. PCT/US2016/051366, dated Dec. 22, 2016.
International Search Report and Written Opinion of the International Searching Authority for PCT application No. PCT/US2016/051380, dated Dec. 26, 2016.
Sogbesan, OA; "Utilization of Treated Duckweed Meal (*Lemna pausicostata*) as Plant Protein Supplement in African Mud Catfish (*Clarias gariepinus*) Juvenile Diets" Fisheries and Aquaculture Journal, vol. 6, Issue 4, ISSN: 2150-3508 FAJ, 2015.
Extended Search Report of European Patent Office in European Patent Application No. 16845295.1, dated Jan. 15, 2019.
Office Action, mailed in Indian Patent Application No. 8948/DELNP/2011 dated Apr. 11, 2018.
Office Action, mailed in Brazilian Patent Application No. P11015000-5, dated Sep. 26, 2018.
Pedroni et al., A Proposal to Establish International Network on Biofixation of CO2 and Greenhouse Gas Abatement with Microalgae, Journal of Energy and Environmental Research, vol. 1, No. 1, Nov. 2001.
http://www.aquaponics.net.au/sites1 O.html, Murray Hallam, Practical Aquaponics for Everyone, Wayback Machine Dec. 2006, 3 pages.
Https://jeremybiggs.wordpress.com/2008/1 0/28/duck-attack/, The Garden Pond Biog, Oct. 2008, 2 pages.
http://collections.infocollections.org/ukedu/en/d/Jii23we/9.1.html, Workshop to produce an Information Kit on Farmer-proven integrated agriculture-aquaculture technologies, IRR; 1992, 10 pages.

Fasakin, E.A. "Nutrient quality of leaf protein concentrates produced from water fern {*Azolla africanna* Desv) and Duckweed {*Spirodela polyrrhiza* L. Schleiden)", Bioresource Technology., vol. 69, No. 2, Aug. 1, 1999 {Aug. 1, 1999), pp. 185-187.
Fowden, L. "The Composition of the Bulk Proteins of Chlorella" [online] Published Jun. 20, 1951. Retrieved fromInternet Jun. 1, 2017: <URL:https://www.ncbi.nlm.nih.gov/pmc/articles/PMC1197660/pdf/biochemj00910-0079.pdf>.
Bolenz, S. et al. "Treatments of Water Hyacinth Tissue to Obtain Useful Products", Biological Wastes, Amsterdam, NL, vol. 33, No. 4, Jan. 1, 1990 {Jan. 1, 1990), pp. 263-274.
Kindel, Paul K. et al. "Solubilization of pectic polysaccharides from the cell walls of Lemna minor and Apium graveolens", Phytochemistry, vol. 41, No. 3, Feb. 1, 1996 {Feb. 1, 1996), GB, pp. 719-723.
Byers, M. "The Amino Acid Composition of Some Leaf Protein Preparations" in IBP Handbook No. 20, Leaf Protein: Its agronomy, Preparation, Quality and Use. 1971, International Biological Programme pp. 95-115.
Kennedy, David "Leaf Concentrate: A Field Guide for Small Scale Programs". Leaf for Life, 1993.
International Search Report and Written Opinion of the International Searching Authority for PCT application No. PCT/U52016/037046, dated Oct. 27. 2016.
International Search Report and Written Opinion of the International Searching Authority (Korean Intellectual PatentOffice) for International Application No. PCT/US2016/041156, dated Oct. 18, 2016.
Freidig et al., Variation in Oxalic Acid Content among Commercial Table Beet Cultivars and Related Crops. Journal of the American Society for Horticultural Science, vol. 136, No. 1, pp. 54-60 (2011).
Extended Search Report in European Patent Application No. 16835862.0, dated Nov. 9, 2018.
Mazen, Ahmed M.A., "Calcium oxalate formation in Lemna minor: physiological and ultrastructural aspects of high capacity calcium sequestration" New Phytologist vol. 161, pp. 435-448, 2003.
International Preliminary Report on Patentability by the International Preliminary Examination Authority (Korean Intellectual Patent Office) for International Application No. PCT/US2016/051366, dated Mar. 22, 2018.
International Preliminary Report on Patentability by the International Preliminary Examination Authority (Korean Intellectual Patent Office) for International Application No. PCT/US2016/051380, dated Mar. 13, 2018.
Titi Mutiara K. et al., 'Effect of blanching treatments against protein content and amino acid drumstick leaves (*Moringa oleifera*)', Journal of Food Research, vol. 2, No. 1, pp. 101-108 (2013).
Gert Jan Schaafsma, 'Advantages and limitations of the protein digestibility-corrected amino acid score (PDCAAS)as a method for evaluating protein quality in human diets', British Journal of Nutrition, vol. 108, pp. S333-S336 (2012).
Extended Search Report in European Patent Application No. 16845285.2 dated Jan. 15, 2019.
Watson, Elaine, "Ultra-fast-growing aquatic plant promises year-round supply of sustainable vegetable protein", Jul. 24, 2015, p. 1-4, XP055537613, www.bakeryandsnacks.com, Retrieved from Internet: URL: www.bakeryandsnacks.com/Article/2015/07/06/Aquatic-plant-promises-year-round-supply-of-sustainable-plant-protein. [Retrieved from Internet on Dec. 21, 2018].
Extended Search Report in European Patent Application No. 16808454.9 dated Feb. 6, 2019.
Kwag, J.H. et al. "Conditions for artificial culture of Lemna Paucicostata and potentiality as an alternative biomass source"; J.Lives.House & Env. 16 (2) pp. 143-152, 2010.

* cited by examiner

METHODS AND SYSTEMS FOR FORMING MOISTURE ABSORBING PRODUCTS FROM A MICROCROP

CROSS-REFERENCE TO RELATED APPLICATIONS

This application claims the benefit of U.S. Provisional Patent Application No. 62/173,645 filed on Jun. 10, 2015 which is incorporated herein by reference in its entirety as set forth in full.

FIELD OF THE DISCLOSURE

The present disclosure relates, in some embodiments, to methods and systems for deriving odor- and moisture-absorbing products from a microcrop (e.g., photosynthetic aquatic species). More specifically, the present disclosure relates, in some embodiments, to forming cat litter and other animal beddings from one or more photosynthetic aquatic species such as *Lemna*. In some embodiments, the present disclosure relates to forming diaper products from one or more photosynthetic aquatic species (e.g., *Lemna*). In other embodiments, the present disclosure relates to forming absorptive products from one or more photosynthetic aquatic species (e.g., *Lemna*). Absorptive products may have a broad range of clean-up applications

BACKGROUND OF THE DISCLOSURE

Due to the practice of animal domestication, people across a broad range of geographical regions and cultures maintain pets that reside within their domiciles or other indoor locations. This has led to a demand for specialized products to aid pet owners in conveniently managing indoor pet care. Litters, for example, are disposable packaged materials designed to deal with animal waste while dispelling odor and enabling expedient (and ideally infrequent) cleanup. Animal beddings are a broader class of products that can provide a natural platform for animals to rest indoors, often in cages.

An ever-increasing global population continues to fuel a plethora of sustainability concerns affecting many pet products including litter (e.g., cat litter) and other beddings (e.g., for rabbit cages). Additionally, concerns relating to climate change and fossil fuel consumption continue to drive innovators to develop more efficient processes for deriving maximum utility from renewable sources.

Existing litters have various limitations and issues that may stem from their compositions. For example, clay-based products may contain silica, which can cause respiratory problems for pets and/or human owners. Furthermore, clay is neither a renewable material nor is it organic in composition. On the other hand, corn-based products may contain carcinogenic substances such as mycotoxins (e.g., aflatoxin). Likewise, wood-based products are also problematic as they can disintegrate and create excessive dust.

Similar sustainability concerns arise regarding the disposal of diaper products (e.g., human diapers, animal diapers, sanitary napkins). The typical disposable diaper is estimated to take over 500 years to degrade through natural processes. Moreover, numerous issues relating to landfills, including the limited availability of space and public health concerns, have been the focus of both government and industry officials. In response, there has been heightened interest in natural (e.g., plant-based, biodegradable) alternatives to those items that take an extended period of time to degrade.

SUMMARY

Accordingly, a need has arisen for improved systems and methods of developing absorptive products (e.g., pet products, diaper products) using renewable sources, such as aquatic species (e.g., a photosynthetic aquatic species) of plants. The present disclosure relates, according to some embodiments, to a process for producing an absorptive product (e.g., animal bedding, diaper product) from a microcrop (e.g., an aquatic species, a photosynthetic aquatic species).

The present disclosure relates, in some embodiments to a process for producing an absorptive product from a microcrop. The process may comprise: lysing a microcrop to generate a lysed microcrop; separating the lysed microcrop into a solid fraction and a juice fraction; processing the solid fraction to generate an absorptive solid. In some embodiments an absorptive solid may comprise an absorptive powder, an absorptive pellet, or an absorptive extrudate. In some embodiments, a microcrop may be *Lemna*.

In some embodiments, processing a solid fraction to generate an absorptive solid may comprise separating the solid fraction to form a solid. A process, according to some embodiments, may further comprise shaping a solid by a shaping unit to generate an absorbent pellet. In some embodiments, a process may further comprise extruding the solid by an extruder to generate the absorbent pellet. According to some embodiments, shaping or extruding a solid may be performed without substantially heating the solid. In some embodiments, shaping or extruding may be performed using steam. According to some embodiments, processing a solid fraction may comprise drying the solid.

According to some embodiments a process may further comprise processing an absorptive solid into an absorptive product. Processing an absorptive solid, in some embodiments, may include packaging the absorptive powder into a porous material that physically contains the absorptive powder while simultaneously allowing external water to freely saturate the absorptive powder.

In some embodiments an absorptive solid may comprises (i) the absorptive solid and (ii) chlorophyll from the microcrop. Chlorophyll may be operable to absorb odor, according to some embodiments. According to some embodiments an absorptive solid may have a moisture content that is less than about 12%, by weight. In some embodiments, an absorptive solid may comprise an absorptive powder having an absorptive coefficient that is ≥about 9.0 L/kg. According to some embodiments an absorptive solid may comprise an absorptive pellet having absorption coefficient that is ≥about 1.44 L/kg.

According to some embodiments, a process may further comprise processing a juice fraction to generate a protein-rich product.

The present disclosure further relates, according to some embodiments, to a process for producing an absorptive product (e.g., animal bedding, diaper product) from a microcrop (e.g., an aquatic species, a photosynthetic aquatic species) that is grown in a bioreactor system. The process may comprise the actions of (a) lysing a microcrop to generate a lysed microcrop; (b) separating the lysed microcrop into a solid fraction and a juice fraction; (c) processing the solid fraction to generate a carbohydrate-rich meal; and (d) processing the carbohydrate-rich meal into an absorptive product, the processing further comprising (i) packaging, in a powdered form, a carbohydrate-rich meal into a porous material that physically contains the powder while allowing (e.g., simultaneously allowing) external water to freely saturate the powder; or (ii) forming (e.g., by a shaping unit) the carbohydrate-rich meal into pellets or granules; or (iii) forming (e.g., by extrusion) the carbohydrate-rich meal into extrudate. According to some embodiments, an absorptive product may comprise (i) a carbohydrate-rich meal and (ii) chlorophyll from a microcrop, where the chlorophyll may be embedded in the pellets and may be operable to absorb odor arising from use of the animal bedding. In some embodiments, an absorptive product may have a moisture content that is less than about 12%, by weight. Lysing a microcrop may comprise using at least one lysing unit selected from the group consisting of a shear mill, a colloid mill, a knife mill, a hammer mill, a grinding mill, a puree machine, a filter press, osmotic pressure, and chemical treatments that degrade biological structures of the microcrop. A lysed microcrop, in some embodiments, may be separated into a solid fraction and a juice fraction using at least one separating unit from the group consisting of a belt press, a decanter centrifuge, a fan press, a rotary press, a screw press, a filter press, a finisher press, a vibratory separator, a vibrating screen filter, a linear or inclined motion shaker, and a high-speed disk stack centrifuge. According to some embodiments, a juice fraction may be processed into a protein rich product (e.g., a human or animal food supplement) that is distinct from an animal bedding. In some embodiments a solid fraction may be processed to generate a carbohydrate-rich meal using at least one drying mechanism selected from the group consisting of a spray dryer, a double drum dryer, a fluid bed dryer, a flash dryer, and a spin flash dryer. A carbohydrate-rich meal may be formed into an absorptive product using steam (e.g., through a steam-based pelletization technique). According to some embodiments, a carbohydrate-rich meal may be formed into an absorptive product without substantially heating the carbohydrate-rich meal. A shaping unit, in some embodiments, may comprise at least one of a pelletizing unit, a granulator, and an extruder. In some embodiments, an absorptive product formed by packaging the powdered form of a carbohydrate-rich meal into a porous package may have an absorption coefficient of ≥10 L/kg. An absorptive product formed by pelletizing or granulating the carbohydrate-rich meal may have an absorption coefficient that is ≥about 1.44 L/kg.

In accordance with some aspects of the disclosure, an animal bedding may be created by processing a microcrop that is grown in a bioreactor system. An animal bedding may comprise pellets comprising chlorophyll from a microcrop, in some embodiments. Chlorophyll may be operable to absorb odor arising from use of the animal bedding. According to some embodiments, pellets may have an average length in a range of about 8-10 millimeters and an average width of about 4 millimeters. In some embodiments, pellets may have a moisture content that is less than about 12%, by weight, and a carbohydrate content that is greater than about 50%, by weight. Pellets, in some embodiments, may have a liquid absorption coefficient greater than or substantially equal to 1.48 liters of liquid per kilogram of pellets. The disclosed techniques for using of a microcrop to derive an animal bedding may provide various benefits. For example, pellets of an animal bedding may remain intact without clumping with each other after being exposed to a liquid, according to some embodiments. In some embodiments, pellets may change in color after being exposed to a liquid and thereby may providing feedback to guide replacement of an animal bedding.

In accordance with some aspects of the disclosure, an animal bedding may comprise an absorbent material comprising an aquatic species (e.g., photosynthetic aquatic species) carbohydrate and an odor-absorbing amount of chlorophyll. For example, an aquatic species (e.g., photosynthetic aquatic species) carbohydrate may be processed from *Lemna*. In some embodiments, an aquatic species (e.g., photosynthetic aquatic species) may be processed from a plurality of different aquatic species (e.g., photosynthetic aquatic species). In some embodiments, at least some of a chlorophyll and at least some of an aquatic species (e.g., photosynthetic aquatic species) carbohydrate may be processed from a common harvest of an aquatic species (e.g., photosynthetic aquatic species). An absorbent material and the chlorophyll may be formed into pellets having a moisture content that is less than about 12%, by weight, according to some embodiments. In accordance with some aspects of the disclosure, a diaper (e.g., a human diaper) may be made, wherein the absorbent layer of the diaper comprises an absorptive product. In some embodiments, an absorptive product may be selected from the group consisting of (i) a package, comprising a porous material and containing carbohydrate-rich meal in a powdered form and chlorophyll from the microcrop, the chlorophyll operable to absorb odor (e.g., odor arising from use of the diaper); (ii) multiple packages, each comprising a porous material and containing carbohydrate-rich meal in a powdered form and chlorophyll from the microcrop, the chlorophyll operable to absorb odor (e.g., odor arising from use of the diaper); (iii) a package, comprising a porous material and containing carbohydrate-rich meal in a pelletized form and chlorophyll from the microcrop, the chlorophyll operable to absorb odor (e.g., odor arising from use of the diaper); and (iv) a package, comprising a porous material and containing carbohydrate-rich meal in a granulated form and chlorophyll from the microcrop, the chlorophyll operable to absorb odor (e.g., arising from use of the diaper). In some embodiments, the package may be quilted to ensure consistent distribution of the powdered carbohydrate-rich meal across the entire area of the package. In some embodiments, the absorbent layer of a diaper may comprise the package as well as other absorbent materials.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

Some embodiments of the disclosure may be understood by referring, in part, to the present disclosure and the accompanying drawings, wherein.

Figure 1A:
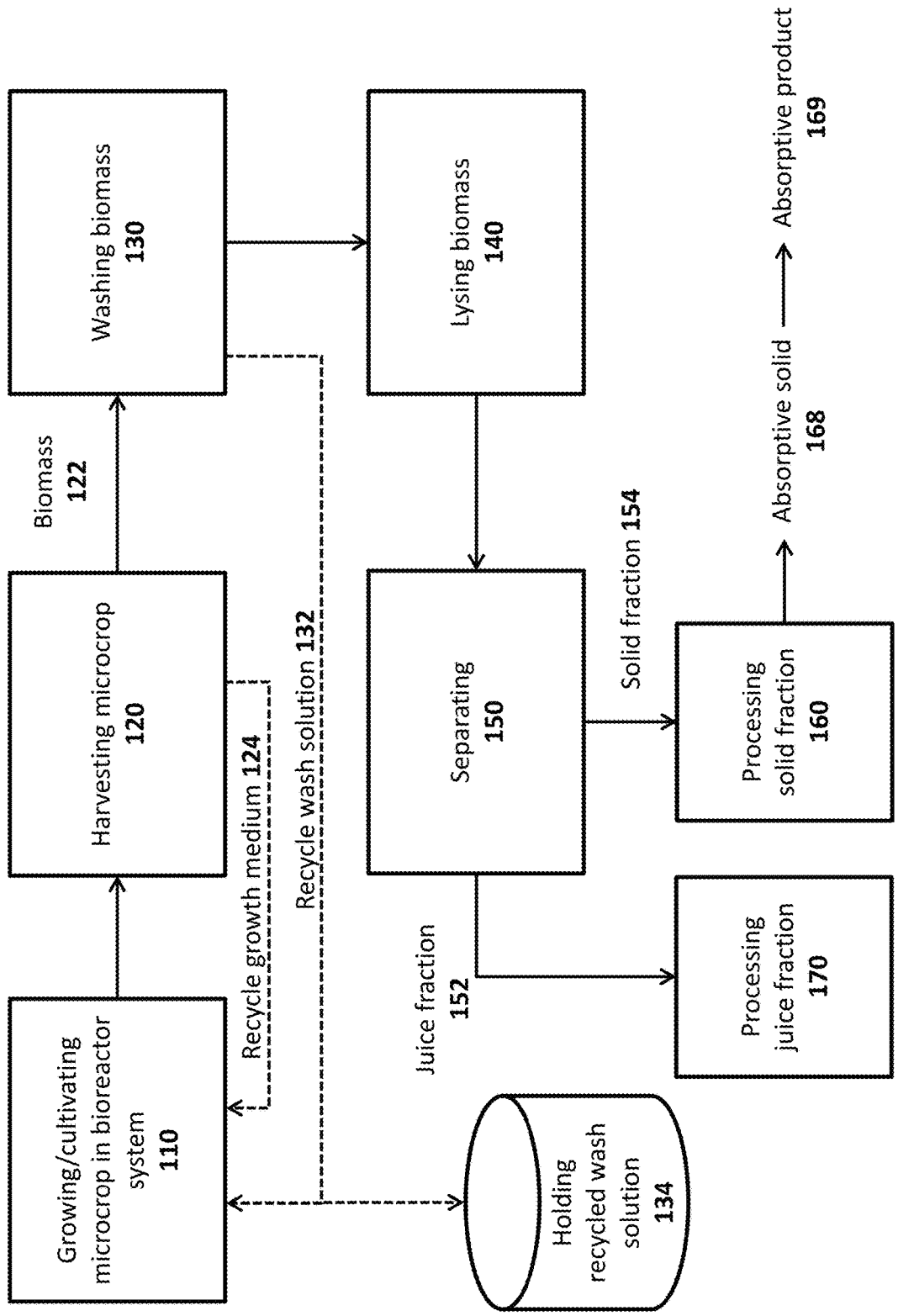
FIG. 1A is a schematic diagram illustrating a process for growing, harvesting, and fractionating a microcrop for the production of animal bedding and other products, according to a specific example embodiment of the disclosure.

These exemplary figures and embodiments are to provide a written, detailed description of the subject matter set forth by any claims in the present application. These exemplary figures and embodiments should not be used to limit the scope of any such claims.

Further, although similar reference numerals may be used to refer to similar structures for convenience, each of the various example embodiments may be considered to be distinct variations. When like reference numerals are used, a description of the common elements may not be repeated, as the functionality of these elements may be the same or similar between embodiments. In addition, the figures are not to scale unless explicitly indicated otherwise.

DETAILED DESCRIPTION

FIG. 1A is a schematic diagram illustrating a process for growing, harvesting, and fractionating a microcrop (e.g., a photosynthetic aquatic species, an aquatic plant species, species of *Lemna*, an algal species) for the production of protein concentrate products and/or carbohydrate-rich products (e.g., an absorptive product), according to a specific example embodiment of the disclosure. A microcrop may be cultivated in a bioreactor system, harvested, and separated to form a solid fraction and a juice fraction. In some embodiments, a solid fraction may be processed to produce one or more carbohydrate-rich products. Additionally or alternatively, a juice fraction may be processed to produce one or more protein concentrate products. Carbohydrate-rich products may include an absorptive product (e.g., an animal bedding, a diaper product). As used herein, the term absorptive product is intended to include products that are capable of absorbing a liquid from their surroundings. In some embodiments an absorptive product may absorb or reduce odors. Due to their moisture- and odor-absorbing properties, carbohydrate-rich products created through the systems and methods described herein may be used in applications such as animal bedding (e.g., animal litter), diaper products, and clean-up applications where the absorption of moisture and odors is advantageous.

Protein concentrate products may include products suitable for animal feed and/or human consumption. A process may be performed indoors, outdoors, and any combination thereof based, for example, on the specific environmental characteristics of a location(s).

In some embodiments, a microcrop may comprise a single photosynthetic aquatic species (e.g., selected from *Lemna*, *Salvinia*, or other suitable genera). A microcrop may comprise, according to some embodiments, a combination of two or more photosynthetic aquatic species. A microcrop may have characteristics that are advantageous in comparison to other photosynthetic aquatic species (e.g., rapid growth rate; reduced nutritional requirements; ease of harvesting and/or processing; reduced evapotranspiration rate; increased carbohydrate composition; increased chlorophyll generation; and other benefits for one or more derived products).

A microcrop may include species of *Lemna* (e.g., duckweed), *Spirodela*, *Landoltia*, *Wolfiella*, *Salvinia* (e.g., floating fern), *Wolffia* (e.g., watermeal), *Azolla* (e.g., mosquito fern), *Pistia* (e.g., water lettuce), or any combination thereof. Exemplary species of *Lemna*, for example, include but are not limited to *Lemna minor*, *Lemna obscura*, *Lemna minuta*, *Lemna gibba*, *Lemna valdiviana*, and *Lemna aequinoctialis*. In some embodiments a microcrop may include one or more algal species. A microcrop may be selected from a local photosynthetic aquatic species based on identified compositional and growth characteristics that have developed within the local environmental conditions. Local species may out-compete other species in open ponds or bioreactors based on their adaptation to the local environmental conditions. A microcrop may be adjusted in response to seasonal variations in temperature and light availability.

In an action 110, a microcrop may be cultivated in a bioreactor system. A bioreactor system may contain a growth medium. A growth medium may comprise water and/or a nutrient composition. A growth medium (e.g., water) may be provided in and/or added to a bioreactor (e.g., a manmade or natural pond) and may be maintained at a desired set-point level. A bioreactor system, in some embodiments, may be configured to collect rainfall and/or to intake water from a source of recycled water (e.g., storm water, recycled water). A bioreactor system may further comprise, according to some embodiments, an additional storage container (e.g., container or pond) for excess growth medium. A bioreactor system may be configured to insert additional nutrients (e.g., nitrogen, phosphorus, potassium) or gases (e.g., oxygen, carbon dioxide) at specified time indicators or in response to sensor readings. In some embodiments, one or more smaller bioreactors (e.g., ponds) may be designed and sized to adequately serve as "feeder" bioreactors to a larger bioreactor. The smaller bioreactors are first inoculated and grown to high density at which point they can optimally seed the larger bioreactor in a manner that supports a more rapid growth.

A bioreactor system may comprise a monitoring system, according to some embodiments. A monitoring system may be configured to display and/or provide one or more user alerts regarding bioreactor condition(s) (e.g., nutrient concentrations, pH, dissolved oxygen levels, growth medium levels, microcrop distribution, flow rate, temperature) and/or adjust operating conditions (e.g., growth medium flow rate and/or timing and/or quantity of nutrient addition; "feeder" microcrop addition, oxygen, or carbon dioxide addition). Adjustments may be made continuously, semi-continuously, periodically, intermittently, as needed, at set or variable times, or any other interval. Adjustments may be selected to optimize growth rates and/or yield of a microcrop (e.g., a photosynthetic aquatic species). For example, a microcrop may be grown in a large-scale, open bioreactor with monitoring systems which adjust the rate of growth medium flow based on exposure to light and rate of production (e.g., photosynthetic rate, reproduction rate) of the microcrop.

In some embodiments, conditions of a bioreactor system (e.g., nutrient composition) may be adjusted to optimize the output of a product derived from or a characteristic of a microcrop. For example, as chlorophyll can serve to improve the odor controllability of absorptive products (e.g., animal beddings) derived from a microcrop, nutrient levels may be adjusted to optimize chlorophyll generation.

A bioreactor system may comprise a single container in which a microcrop is cultivated. In some embodiments, a bioreactor system may comprise a plurality of cultivation containers that may be connected, partially connected, or disconnected. In some embodiments, a bioreactor (e.g., pond) may be an earthen basin with the embankments composed of compacted dirt (e.g., removed from the interior bottom of the bioreactor). In some embodiments a bioreactor may be an artificial container (e.g., metal, plastic, resin). A bioreactor system may comprise an open bioreactor, a closed bioreactor, a semi-open bioreactor, or any combination thereof. A bioreactor system may be configured to divide the container(s) into channels or cells. In some embodiments a bioreactor system may be configured to permit a flow of growth medium. A bioreactor system may include propulsion systems (e.g., paddle wheels, bubbling, submerged or surface water jets, submerged mixers) and/or recirculation systems, according to some embodiments. A bioreactor system, in some embodiments, may be configured to adjust a flow rate of a growth medium (e.g., to redistribute nutrient concentrations or microcrop growth patterns).

A bioreactor system may be configured to monitor and adjust a thickness or a distribution of a microcrop mat. For example, when a microcrop reaches a specified thickness or a specified distribution, a bioreactor system may be configured to initiate harvest procedures. In some embodiments, a bioreactor system may be configured to maintain a minimum thickness of a microcrop mat so as to reduce evapotranspiration rates of a growth medium within the bioreactor system. In some embodiments, a bioreactor system may be configured to maintain a minimum thickness of a microcrop mat so as to reduce a level of sunlight capable of penetrating a growth medium, thereby reducing a growth of submerged photosynthetic aquatic species such as algae.

In an action 120, at specified times (e.g., based on environmental conditions) or after a microcrop develops specified characteristics (e.g., mat thickness, mat distribution, maturation) the microcrop may be harvested from a bioreactor system, forming a biomass 122. Harvesting of a microcrop may be manual or automated. In some embodiments, an automated skimmer system may collect a microcrop from a bioreactor system and transfer a harvested microcrop (e.g., via a pumping system) onto an inclined vibrating screen to separate a biomass 122 from growth medium and debris. A microcrop, in some embodiments, may be harvested by vacuum skimming the microcrop from a bioreactor system through a stationary screen filter. In some embodiments, a biomass slurry, including a harvested microcrop (e.g., *Lemna*) and a growth medium (e.g., water), can be conveyed to an inclined vibrating screen where a biomass may be separated from the growth medium.

During harvesting, a separated growth medium may be recycled 124 back into a bioreactor system or to an additional storage container (e.g., container or pond). At least 40%, or at least 50%, or at least 60%, or at least 70%, or at least 80%, or at least 90%, or at least 95% of a growth medium (e.g., water) separated from a biomass may be recycled 124 for future use.

In an action 130, a biomass may be subjected to a wash procedure configured to remove debris, contaminants, microorganisms, and/or toxins. Washing a biomass may increase protein and/or carbohydrate yield, thereby improving end products. A wash procedure may also disinfect and/or disinfest a biomass, reducing the amount of bacteria, fungi, viruses, insects, or any combination thereof which may be on or around one or more surfaces of the biomass. In some embodiments, a wash procedure may be performed by exposing (e.g., submerging, spraying) one or more surfaces of a biomass to a wash solution (e.g., water, growth medium, antimicrobial solution). A wash solution may be an aqueous solution or a solvent, according to some embodiments. In some embodiments, a wash solution may contain one or more antimicrobial compounds, fatty acids, alcohols, chlorine, oxidizing compounds, or any combination thereof. A wash solution, in some embodiments, may be applied at an elevated temperature and/or at an increased pressure. In some embodiments, a wash solution may remain in contact with one or more surfaces of a biomass for at least 1 second, or for at least 5 seconds, or for at least 10 seconds, or for at least 20 seconds, or for at least 30 seconds, or for at least 1 minute, or for at least 5 minutes. According to some embodiments, a second wash solution may be applied to one or more surfaces of a biomass. A second wash solution, in some embodiments, may be an aqueous solution (e.g., water) or a solvent. In some embodiments, some or all of a wash solution and/or a second wash solution may be separated from a biomass (e.g., using an inclined screen or vibratory screen).

In some embodiments, some or all of a wash solution and/or a second wash solution may be collected and reused (e.g., recycled). At least 40%, or at least 50%, or at least 60%, or at least 70%, or at least 80%, or at least 90%, or at least 95% of a wash solution and/or a second wash solution (e.g., water) separated from a biomass may be recycled 132 for future use, according to some embodiments. For example, at an action 134, a recycled wash solution may be held (e.g., in a wash solution container) for any desired time and then reincorporated, either manually or automatically, into a bioreactor system of action 110.

In some embodiments, at an action 140, a biomass, either washed or unwashed, may be lysed to form a lysed biomass. Lysing may include, for example, chopping, shredding, smashing, pressing, tearing, shearing, lysis by osmotic pressure, ultrasonic treatments (e.g., sonication), or chemical treatments (e.g., pH adjustment) that degrade biological structures. In some embodiments, lysing may be achieved in a mechanical way (also referred to as milling), for example, by milling, grinding, or shredding a biomass to generate a lysed biomass. A lysing process, in some embodiments, may be achieved using, for example, a shear mill, a ball mill, a colloid mill, a knife mill, a hammer mill, a grinding mill, a puree machine, a filter press, or any combination thereof.

In some embodiments, lysing may be performed at temperatures below room temperature (e.g., about 12° C.). A lysing fluid (e.g., water, recycled water, reverse osmosis water) may be added to a biomass or a microcrop before or during lysing, according to some embodiments. For example, at least about 10%, at least about 20%, at least about 30%, at least about 40%, at least about 50%, at least about 60%, at least about 70%, at least about 80%, or at least about 90% of a lysing fluid may be reverse osmosis water generated as the result of reverse osmosis/nanofiltration of a filtration product. In some embodiments a lysing fluid may be at a temperature below room temperature (e.g., about 12° C.).

At an action 150, a lysed biomass (e.g., comprising a microcrop) may be separated to form a juice fraction 152 and a solid fraction 154. In some embodiments, a biomass (e.g., comprising a washed or an unwashed microcrop) is separated 150 to form a juice fraction 152 and a solid fraction 154, before or without a lysing action 140. Separating 150 a lysed biomass or a biomass may involve pressing (e.g., by belt press), centrifugation, filtration, pressurized filtration, or any combination thereof. In some embodiments, interchangeable unit operations for separating a lysed or an unlysed biomass include, for example, a decanter centrifuge, a belt press, a fan press, a rotary press, a screw press, a filter press, a finisher press, or any combination thereof.

Figure 1B:
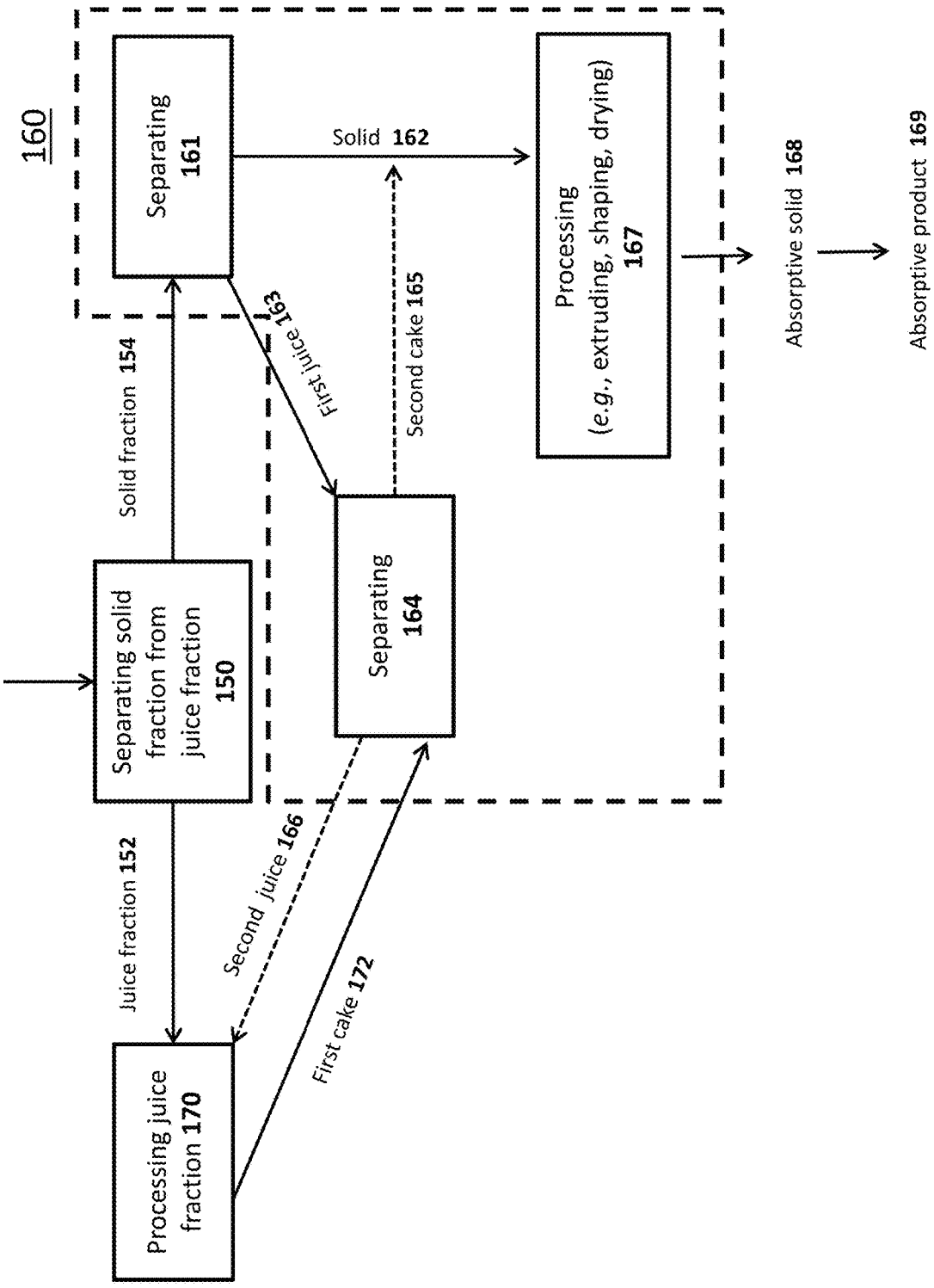
FIG. 1B is a schematic diagram illustrating a process for separating a biomass to form a juice fraction and a solid fraction, processing a juice fraction, and processing the solid fraction, according to a specific example embodiment of the disclosure.

At action 160, a solid fraction 154 may be further processed (e.g., separating, extruding, shaping, heating, drying, milling) to form an absorptive solid 168 (e.g., an absorptive pellet, an absorptive powder, an absorptive exudate) (see, e.g., FIG. 1B). In some embodiments, an absorptive solid 168 (e.g., an absorptive pellet, an absorptive powder, absorptive exudate) may be directly used as an absorptive product (e.g., animal litter, animal bedding, spill clean-up product). According to some embodiments, an absorptive solid 168 (e.g., an absorptive pellet, an absorptive powder) may be further processed to generate an absorptive product 169 (e.g., diaper product, animal bedding, animal litter).

At an action 170, a juice fraction 152 may be further processed to arrive at a separate product (e.g., a protein concentrate for nutritional supplementation). This product may have utility that is distinct from that of the solid fraction-based products, and accordingly, the total utilization and profitability of the harvested microcrop may increase.

While various actions are shown in FIG. 1A, more, fewer, or different actions may be performed to process a microcrop and form an absorptive product. For example, an action 170 for processing a juice fraction may not be performed in some embodiments, and the juice fraction may instead be discarded or recycled into a bioreactor system (e.g., to provide nutrients to a microcrop that has not yet been harvested). Furthermore, and as will be shown in the examples below, the order of the actions may vary.

In some embodiments, a process for growing, harvesting, and separating a microcrop (e.g., photosynthetic aquatic species, Lemna, algal species) may entail multiple cycles or a continuous process for production of absorptive solids such that byproducts of an earlier cycle of the process may be recycled into one or more subsequent cycles of a process. Recycling of one or more by-products may reduce the overall water requirement for a process. In some embodiments, a continuous or cyclical process may be configured to minimize a net energy input required to produce a quantity of absorptive solid.

Figure 1C:
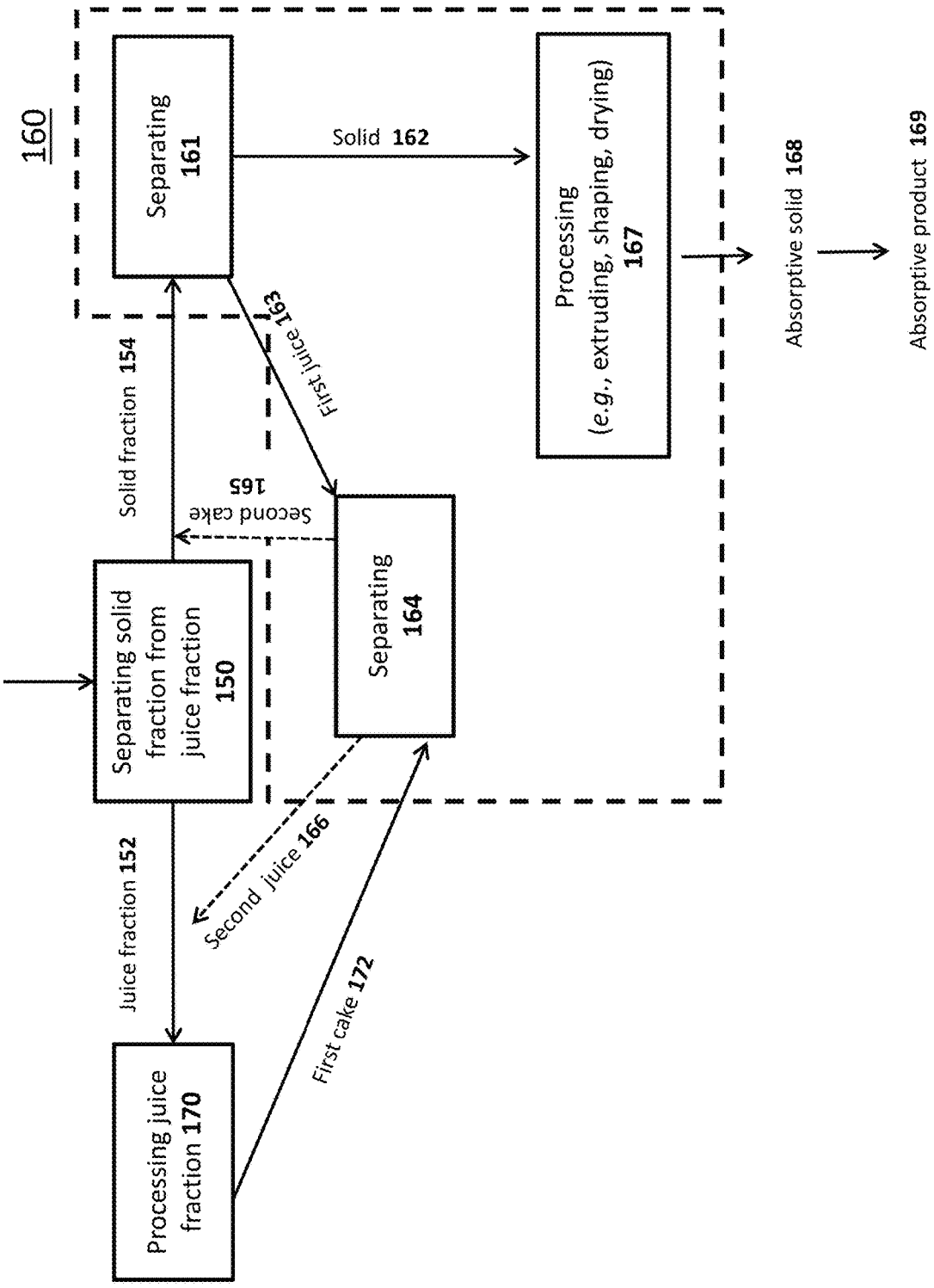
FIG. 1C is a schematic diagram illustrating the separation of a solid fraction from a juice fraction and processing the solid fraction for the production of carbohydrate-rich products according to a specific example embodiment of the disclosure.

FIG. 1B and FIG. 1C are each a schematic diagram illustrating a process for separating a biomass 122 to form a juice fraction 152 and a solid fraction 154, processing a juice fraction 170, and processing the solid fraction 160, according to specific example embodiments of the disclosure.

Separating a Biomass

As shown in FIG. 1B and FIG. 1C, a biomass 122 may be separated 150 to generate a juice fraction 152 and a solid fraction 154. In some embodiments, a biomass (e.g., Lemna) 122 to be separated 150 may be washed, unwashed, lysed, unlysed, or any combination thereof. A juice fraction 152 may include a protein rich liquid and/or at least some solid particles (e.g., carbohydrates, fiber).

Separating 150 a biomass 122, which may have been previously washed and/or lysed, may involve pressing (e.g., belt press), centrifugation, filtration, pressurized filtration, or any combination thereof. Interchangeable unit operations for separating 150 a biomass (e.g., a harvested microcrop), a washed biomass, and/or a lysed biomass include, for example, a decanter centrifuge, a belt press, a fan press, a rotary press, a screw press, a filter press, a finisher press, or any combination thereof.

Separating 150 may be performed at temperatures below room temperature (e.g., 12° C.), for example, to decrease proteolytic activity. In some embodiments, separating may be performed at a temperature below about 40° C., below about 30° C., or below about 20° C., or below about 15° C., or below about 10° C., or below about 15° C., or below about 10° C., or below about 5° C., or below about 2° C., or below about 1° C., or below about 0° C. Separating 225 may be performed at any desired temperature, for example, at a temperature between about 0° C. and about 10° C., or between about 5° C. and about 15° C., or between about 10° C. and about 20° C., or between about 15° C. and about 25° C., or between about 20° C. and about 30° C., or between about 25° C. and about 35° C., or between about 30° C. and about 40° C.

Separating a Solid Fraction

As shown in FIG. 1B and FIG. 1C, a solid fraction 154 may be further processed 160 to generate a solid 162. In some embodiments, a solid fraction 154 may be separated 161 to extract additional juice, forming a first juice 163 and a solid 162. In some embodiments, a first juice 163 may include a protein rich liquid and/or at least some solid particles (e.g., carbohydrates, fiber).

Separating 161 a solid fraction 154 to form a first juice 163 and a solid 162 may involve pressing (e.g., belt press), centrifugation, filtration, pressurized filtration, or any combination thereof. Interchangeable unit operations for separating 161 a solid fraction include, for example, a decanter centrifuge, a belt press, a fan press, a rotary press, a screw press, a filter press, a finisher press, or any combination thereof.

In some embodiments, as shown in FIG. 1B and FIG. 1C for example, other solid fractions (e.g., a first cake 172, a second cake 165) which are collected at other stages in a process (e.g., processing of a juice fraction yields a first cake) may be combined with a solid 162 to form a solid mixture. According to some embodiments a solid 162 or a solid mixture may be further processed 167 (e.g., by drying, shaping, extruding, or any combination thereof) to form an absorptive solid 168.

In some embodiments, a moisture content of a solid 162 and/or solid mixture may be less than about 90%, or less than about 80%, or less than about 70%, or less than about 60%, or less than about 50%, or less than about 40%, or less than about 30%, or less than about 20%, or less than about 10% by weight.

Recycling when Processing a Juice Fraction and/or a Solid Fraction

As shown in FIG. 1B and FIG. 1C, a juice fraction 152 may be processed 170 to generate a first cake 172. A first cake 172 may be a solid material comprising carbohydrates and/or chlorophyll that were not initially separated (e.g., at the action 150) to be part of a solid fraction 154. That is, a first cake 172 may be formed from at least some of the solids remaining in a juice fraction 152.

In some embodiments, as shown in FIG. 1B and FIG. 1C, a first cake 172 and a first juice 163 may be combined and further separated 164 to form a second juice 166 and a second cake 165. According to some embodiments, a first cake 172 and a first juice 163 may be independently subjected to further separation 164.

According to some embodiments, one or both of a second juice 166 and a second cake 165 collected in one cycle may be fed back to be further processed in a subsequent cycle. For example, as shown in FIG. 1C a second cake 165 produced and collected from one cycle may be fed back to be combined with a solid fraction 154 of a subsequent cycle. Additionally or alternatively, as shown in FIG. 1C, a second juice 166 produced and collected from one cycle may be fed back to be combined with a juice fraction 152 of a subsequent cycle. In some embodiments, a separation action 164 may be bypassed, such that a first cake 172 resulting from processing a juice fraction 152 at an action 170 may be directly combined with a solid fraction 154 or a solid 162 of a subsequent cycle. Likewise, in some embodiments, a first juice 163 from separating a solid fraction 154 at an action 161 may be directly combined with a juice fraction 154 of a subsequent cycle. In some embodiments, a process may be continuous such that there are not discrete cycles. In these embodiments, outputs from one processing unit or action may be continuously provided as inputs to other processing units.

According to some embodiments, a unit(s) for separating 154 a solid fraction and/or processing 170 a juice fraction may require or benefit from a particular range of moisture contents and/or solid-to-juice ratios. Accordingly, a second juice 166 and/or a second cake 165 may be fed back to a unit(s) for separating 161 a solid fraction and/or processing 170 a juice fraction such that a net input to each of these unit(s) falls within a suitable range. This may beneficially reduce stress placed on one or more unit(s), thereby increasing their usable lifetime(s). It may also beneficially maximize a total effective separation of a juice fraction 152 and a solid fraction 154.

According to some embodiments, a first cake 172 and a first juice 163 may be independently subjected to further separation 164. Separating 164 a first cake 172, a first juice 163, or any combination thereof may involve centrifugation, filtration, pressurized filtration, or any combination thereof, in some embodiments. Several different interchangeable unit operations may be used to separate 164 including, for example, a high-speed disc stack centrifuge, a circular vibratory separator, a linear/inclined motion shaker, a decanter centrifuge, a filter press, pressurized filtration mechanisms, microfiltration, vacuum filtration, or any combination thereof.

Separating 164 may be performed, according to some embodiments, at temperatures below room temperature, for example, to decrease proteolytic activity. In some embodiments separating 164 may be performed at a temperature below about 40° C., or below about 30° C., or below about 20° C., or below about 15° C., or below about 10° C., or below about 15° C., or below about 10° C., or below about 5° C., or below about 2° C., or below about 1° C., or below about 0° C. Separating 164 may be performed at a temperature between about 0° C. and about 10° C., or between about 5° C. and about 15° C., or between about 10° C. and about 20° C., or between about 15° C. and about 25° C., or between about 20° C. and about 30° C., or between about 25° C. and about 35° C., or between about 30° C. and about 40° C., in some embodiments.

As shown in FIG. 1B, a second cake 165 may be combined with a solid 162 to form a solid mixture, in some embodiments. As shown in FIG. 1C, a second cake 165 may be combined with a solid fraction 154 (e.g., of a subsequent cycle of processing) to form a solid mixture. A solid mixture may be subjected to further processing (e.g., separating 161, processing 167).

According to some embodiments, for example as shown in FIG. 1B, a second juice 165 may be further processed 170. As shown in FIG. 1C, a second juice 165 may be combined with a juice fraction 152 (e.g., of a subsequent cycle of processing).

Processing a Solid and/or a Solid Mixture

As shown in FIG. 1B and FIG. 1C, at action 167, a solid 162 and/or a solid mixture may be further processed (e.g., shaping, extruding, drying, heating, milling) to form an absorptive solid 168 (e.g., an absorptive pellet, an absorptive powder, an absorptive exudate). In some embodiments, an absorptive solid 168 (e.g., an absorptive pellet, an absorptive powder, absorptive exudate) may be directly used as an absorptive product 169 (e.g., animal litter, animal bedding, spill clean-up product). Absorbent solids may also be suitable as a fuel feedstock or a carbohydrate-rich meal suitable as a human or animal feed supplement (e.g., *Lemna* meal).

As described previously, a solid mixture may include one or more of a solid 162, a first cake 172, a second cake 165, or any combination thereof that remain after one or more separation processes 150/161/170/164. A process for generating an absorptive solid may be varied depending upon the specific characteristics desired, including, for example, moisture content, particle size, protein content, fat content, fiber content, ash content, chlorophyll content, shelf-life, pellet or granule size and shape, texture, or any combination thereof.

Drying

In some embodiments, a solid 162 and/or a solid mixture may be subjected to a drying procedure by a drying unit to reduce a moisture content of a resulting absorptive solid 168. A drying procedure, in some embodiments, may be performed in conjunction with, prior to, or following other processing (e.g., milling, pelletization, extrusion) of a solid 168 and/or a solid mixture, such that an end product is a absorptive solid with a reduced moisture content. A drying procedure may be performed, in some embodiments, using a dryer mechanism including, for example, a spray dryer, double drum dryer, flash dryer, evaporator, or any combination thereof.

According to some embodiments, a drying process may be coupled with another processing step (e.g., shaping, extruding, milling), wherein a separated 161 solid is dried while simultaneously being processed (e.g. shaping, pelletizing 166, or extruding 167) into an absorptive solid 168 (e.g. absorptive pellet, absorptive extrudate, absorptive granule).

In some embodiments, after a drying procedure, a solid and/or a solid mixture may be further processed to form an absorptive solid which may be used in a powdered form directly as an absorptive product (e.g. spill clean-up applications). A dried solid and/or solid mixture, in some embodiments, may be shaped 237 by a shaping unit, which may comprise a pelletization machine, a granulator, or other apparatus for shaping the solid 231 and/or solid mixture into groupings (e.g., pellets or granules) that are suitable or convenient for use in or as an absorptive product (e.g. spill clean-up applications, animal bedding). A shaping procedure 237 may result in multiple pellets, granules, or other types of clusters (e.g., of an absorptive solid) which may have a regular shape (e.g., cylindrical or spherical) that are roughly homogenous (e.g., having similar lengths and cross-sectional diameters if cylindrical or having similar diameters if spherical), according to some embodiments. In some embodiments, a shaping 237 may result in heterogeneous and/or irregularly shaped clusters that make up an absorptive product. According to some embodiments, a solid 231 and/or solid mixture may become a final product (e.g. absorptive powder) simply through a drying procedure 235 (e.g., where it is not desired that an absorptive product be shaped).

Milling

According to some embodiments, a solid 162 and/or a solid mixture may be milled to form an absorptive powder (e.g., having a reduced particle size). In some embodiments, a solid 162 and/or a solid mixture may be milled prior to drying. According to some embodiments, a solid 162 and/or a solid mixture may be milled where the solid 162 and/or the solid mixture retains a moisture content of <99%, or <90%, or <80%, or <70%, or <60%, or <50%, or <40%, or <30%, or <20%, or <10%, or <5%, or <4%, or <3%, or <2%, or <1%. A solid 162 and/or a solid mixture may be milled using, for example, a shear mill, or knife mill, Colloid mill, hammer mill, grinding mill, puree machine, filter press, sonication.

Shaping

According to some embodiments, a solid 162 and/or a solid mixture may be shaped (e.g., granulation or pelletization) by a shaping unit to form a pellet. A pellet may be used directly as an absorptive product such as animal litter, animal bedding, or as a spill clean-up applications, according to some embodiments. In some embodiments, a pellet may form a component of an absorptive product, such as an absorbent core of a diaper product (e.g., human or animal diaper, sanitary napkin).

A shaping unit, according to some embodiments may comprise a pelletization machine, a granulator, or other apparatus for shaping a solid 162 and/or a solid mixture into groupings (e.g., pellets or granules) that are suitable or convenient for use in or as an absorptive product (e.g. animal litter, spill clean-up applications, animal bedding, absorbent core of a diaper product). A shaping procedure may result in multiple pellets, granules, or other types of clusters (e.g., of an absorptive solid) which may have a regular shape (e.g., cylindrical or spherical) that are roughly homogenous (e.g., having similar lengths and cross-sectional diameters if cylindrical or having similar diameters if spherical), according to some embodiments. In some embodiments, a shaping procedure may result in heterogeneous and/or irregularly shaped clusters that make up a pellet.

Other shaping units may be employed in processing a solid 162 and/or a solid mixture into an absorptive solid having different shapes (e.g., disks, spheres, extruded cylinders) and/or powdered forms. In some embodiments it may be advantageous to process an absorptive solid into granules. Granulation may be accomplished in conjunction with a drying process by using a fluid bed dryer whose parameters are adjusted to deliver a granular output instead of a powder output. In other embodiments, a dried powder may be subject to a granulation process as a separate processing step.

A shaping unit may be a pellet mill that uses a flat die, a ring die, or any other type of mechanism to extrude cylindrical portions of an absorptive solid (e.g., chemically modified or unmodified), according to some embodiments. One or more blades may be used to cut a cylindrical portions as they are extruded, thereby forming a plurality of pellets. In some embodiments, a pellet may have a width of about 4 millimeters (mm) and a length in a range of about 8 mm to about 10 mm. However, larger, smaller, or differently proportioned pellets may also be generated depending, e.g., on the intended use. These dimensions may be established based on factors of a shaping unit, such as die type and cutting frequency. A shaping unit may be tunable to vary the dimensions of pellets, or it may be interchanged with a different shaping unit.

In some embodiments a shaping procedure may include the use of heat, steam, and/or drying to form a pellet. Due to the unique chemical properties of some microcrops, such as *Lemna*, a shaping unit may not require heat in some embodiments. By allowing for a shaping process to begin without waiting for shaping unit (e.g., a pelletizing unit) to heat up, a shaping process may result in energy conservation and/or production control benefits (e.g., where the shaping unit is not operating continuously). In some embodiments, a shaping unit (e.g., a pelletizing unit) may not substantially heat or change a composition of pellet. A pelletizing unit, in some embodiments, may apply heat and/or a binding agent to form pellets and may thus alter a chemical composition of an absorptive solid (e.g., by lowering the moisture content). Steam may be used to produce a firmer pellet if desired, which may also increase a moisture content.

In some embodiments, a shaping unit may be integrated with a dryer, such that an output of the combined drying and shaping unit is an absorptive product (e.g., animal litter, animal bedding, spill clean-up product). According to some embodiments, a pellet may form a component of an absorptive product (e.g., absorbent core of a diaper product).

Extruding

According to some embodiments, a solid 162 and/or a solid mixture may be processed by an extruder. In some embodiments, an extruder process may involve treating a solid 162 and/or a solid mixture with a combination of heat, pressure and water inside an extruder device to generate an absorptive solid that may have altered (e.g., improved) texture and/or porosity.

In some embodiments, an extruder may be employed during processing to extrude segments (e.g., extrudate) of an absorptive product having a generally constant cross-section. An extruder may use a flat die, a ring die, or any other type of mechanism to extrude cylindrical portions of modified or unmodified absorptive solid, according to some embodiments. One or more blades may be used to cut a cylindrical portions as they are extruded, thereby forming extrudates (e.g., extrudate). In some embodiments, extrudates may have a width of about 4 millimeters (mm) and a length in a range of about 8 mm to about 10 mm. However, larger, smaller, or differently proportioned extrudates may also be generated depending, e.g., on the intended usage scenarios. These dimensions may be established based on factors of an extruder, such as die type and cutting frequency. An extruder may be tunable to vary the dimensions of extrudates, or it may be interchanged with a different extruder.

According to some embodiments, an extrudate may be further subjected to a drying procedure. In some embodiments, a drying process and an extruding process may be performed simultaneously or concurrently.

Absorptive Products

In some embodiments, an absorptive powder 164 may be directly used as an absorptive product 169 (e.g. spill clean-up). According to some embodiments, an absorptive powder, an absorptive pellet, or an absorptive extrudate may be directly used as an absorptive product without further processing. For example, an absorptive powder, an absorptive pellet, an absorptive extrudate, or a combination thereof may be used as a spill clean-up product, an animal litter, or an animal bedding, according to some embodiments.

According to some embodiments, an absorptive solid 168 (e.g., an absorptive pellet, an absorptive powder) may be further processed to generate an absorptive product 169 (e.g., diaper product, animal bedding, animal litter).

In some embodiments, an absorptive solid (e.g., an absorptive powder, an absorptive pellet, an absorptive exudate) may be packaged into a porous material that physically contains the absorptive solid while simultaneously allowing external liquid to freely saturate the absorptive solid. In some embodiments, a packaged solid and/or solid mixture may resemble a large tea bag. In other embodiments, a packaged solid and/or solid mixture may resemble several small tea bags. In some embodiments, a porous packaging may comprise paper, or cotton, or other porous material. In other embodiments, a porous packaging may comprise any combination of paper, cotton, or other porous or biodegradable material. A porous packaging, in some embodiments, may include any appropriate material including natural fiber, porous plastic, polymer composition, or any combination thereof. According to some embodiments, a bulk density of a powder may be about 400 kg/m$^3$, or about 350 kg/m$^3$ to about 450 kg/m$^3$, or about 300 kg/m$^3$ to about 500 kg/m$^3$, about 0.4 g/cm$^3$, or about 0.35 g/cm$^3$ to about 0.45 g/cm$^3$, or about 0.3 g/cm$^3$ to about 0.5 g/cm$^3$.

In some embodiments, an absorptive powder may be further processed to form an absorptive pellet or an absorptive exudate. According to some embodiments, an absorptive powder may be processed by a shaping unit (e.g., pelletizer, granulator, extruder) to form an absorptive pellet or absorptive extrudate. In some embodiments, a shaping process may be performed without heating an absorptive powder. According to some embodiments, a shaping process may include an application of steam to an absorptive powder, an absorptive pellet, or an absorptive extrudate. An application of steam during a shaping process may help an absorptive pellet or an absorptive extrudate to better maintain its shape or decrease its proclivity to crumble.

In other embodiments, an absorptive solid 168 (e.g. absorptive pellet, absorptive extrudate, absorbent powder) may be processed to form an absorptive product 169. Absorptive products 169 may include animal litter, diaper products (e.g. human diaper, animal diaper, sanitary napkins, wound stuffing, other diaper products), spill clean-up products, or other products which may be used to absorb liquid or moisture.

Figure 1D:
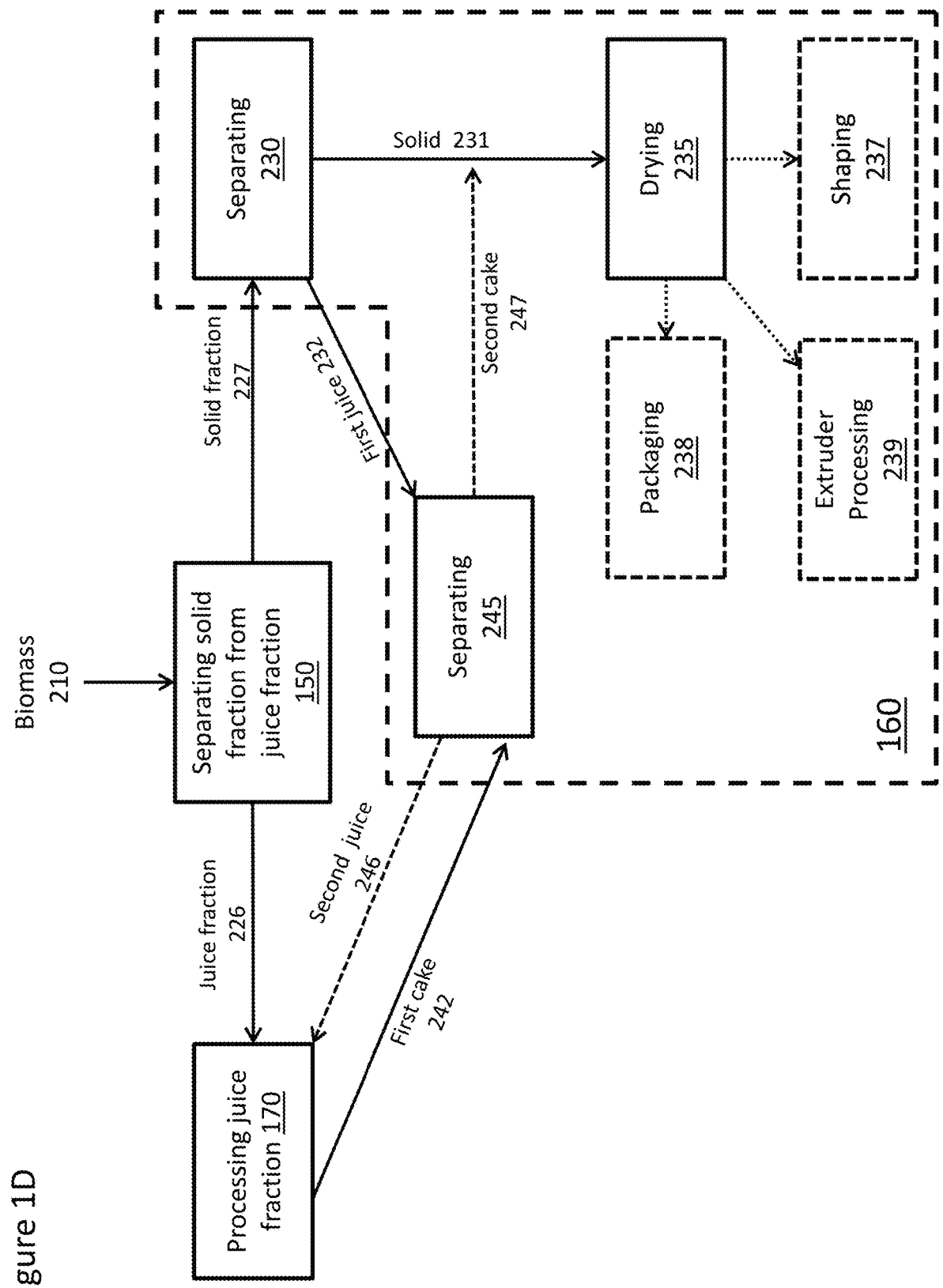
FIG. 1D is a schematic diagram illustrating the separation of a solid fraction from a juice fraction and processing the solid fraction for the production of carbohydrate-rich products according to a specific example embodiment of the disclosure.

FIG. 1D illustrates a processing action of a solid fraction into an absorptive product according to a specific example embodiment of the disclosure. A processing action 160, in some embodiments, may include pressing, separating 245, and/or drying 235 a solid fraction 227 to generate an absorptive powder. An absorptive powder may have a reduced moisture content and/or a reduced soluble protein content when compared with a solid fraction. An absorptive powder may have an increased carbohydrate concentration (w/v, w/w) when compared to a solid fraction 227 and may be considered a absorptive solid. In some embodiments, a drying unit may be used to dry 235 (e.g., partially dry, completely dry) a solid fraction 227. A drying unit may comprise a spray dryer, a drum dryer, a flash dryer, a spin flash dryer, a fluid bed dryer, or any combination thereof.

According to some embodiments, drying and/or pressing may additionally or alternatively occur at a separating action 150 previously described. In some embodiments, a drying process may be coupled with a processing step, wherein a separated solid 231 is dried while simultaneously being processed (e.g. shaping, pelletizing 237, or extruding 239) into an absorptive solid (e.g. absorptive pellet, absorptive extrudate, absorptive granule).

In some embodiments, an absorptive powder may be directly used as an absorptive product (e.g. spill clean-up). In other embodiments, an absorptive powder may be processed by a shaping unit (e.g., pelletizer 237, granulator, extruder 239) to form an absorptive solid (e.g. absorptive pellet, absorptive extrudate, absorptive granule). In some embodiments, a shaping process may be performed without heating an absorptive powder or separated 231 solid. In some embodiments, a shaping process may be performed on a solid fraction that has not undergone a drying process. According to some embodiments, a shaping process may include an application of steam to a absorptive powder or separated solid 231 or an absorptive solid (e.g. absorptive pellet, absorptive extrudate, absorptive granule). An application of steam during a shaping process may help an absorptive solid to better maintain its shape or decrease its proclivity to crumble.

In some embodiments, an absorptive solid may be used directly as an absorptive product (e.g. animal litter, spill clean-up applications) without additional processing (e.g. packaging, forming). In other embodiments, an absorptive solid (e.g. absorptive pellet, absorptive extrudate, absorptive granule, absorbent powder) may be processed to form an absorptive product. Absorptive products may include animal litter, diaper products (e.g. human diaper, animal diaper, sanitary napkins, wound stuffing, other diaper products), spill clean-up products, or other products which may be used to absorb liquid or moisture. Shaping and/or extrusion of an absorptive solid may be performed prior to or concurrently with drying to form an absorptive product.

An absorptive product, in some embodiments, may have an absorbent material comprising carbohydrate from a microcrop (e.g., an photosynthetic aquatic species) and an odor-absorbing amount of chlorophyll, at least some of which may also be from the microcrop. In some embodiments, an odor-absorbing amount may be an amount that reduces the odor perceived by one or more humans, which may or may not be assessed through a rigorous sensory analysis. An odor-absorbing amount, in some embodiments, may refer to an amount that reduces the amount of airborne odor-causing particles detectable by any suitable assay. According to some embodiments, an odor-absorbing amount may comprise a wide range of concentrations. For example, a absorptive solid used to generate an absorptive product may comprise a chlorophyll concentration of at least about 50 mg/kg. In some embodiments, a chlorophyll concentration of a carbohydrate-rich solid may be about 150 mg/kg. Other suitable chlorophyll concentrations may be appropriate for absorbing odor. A chlorophyll concentration of an photosynthetic aquatic species used to derive an absorptive product may also vary. For example, dried *Lemna* may have a chlorophyll concentration of about 850 mg/kg.

While various actions are shown in FIG. 1D, more, fewer, or different actions may be performed to process a microcrop and form an absorptive product.

Figure 1E:
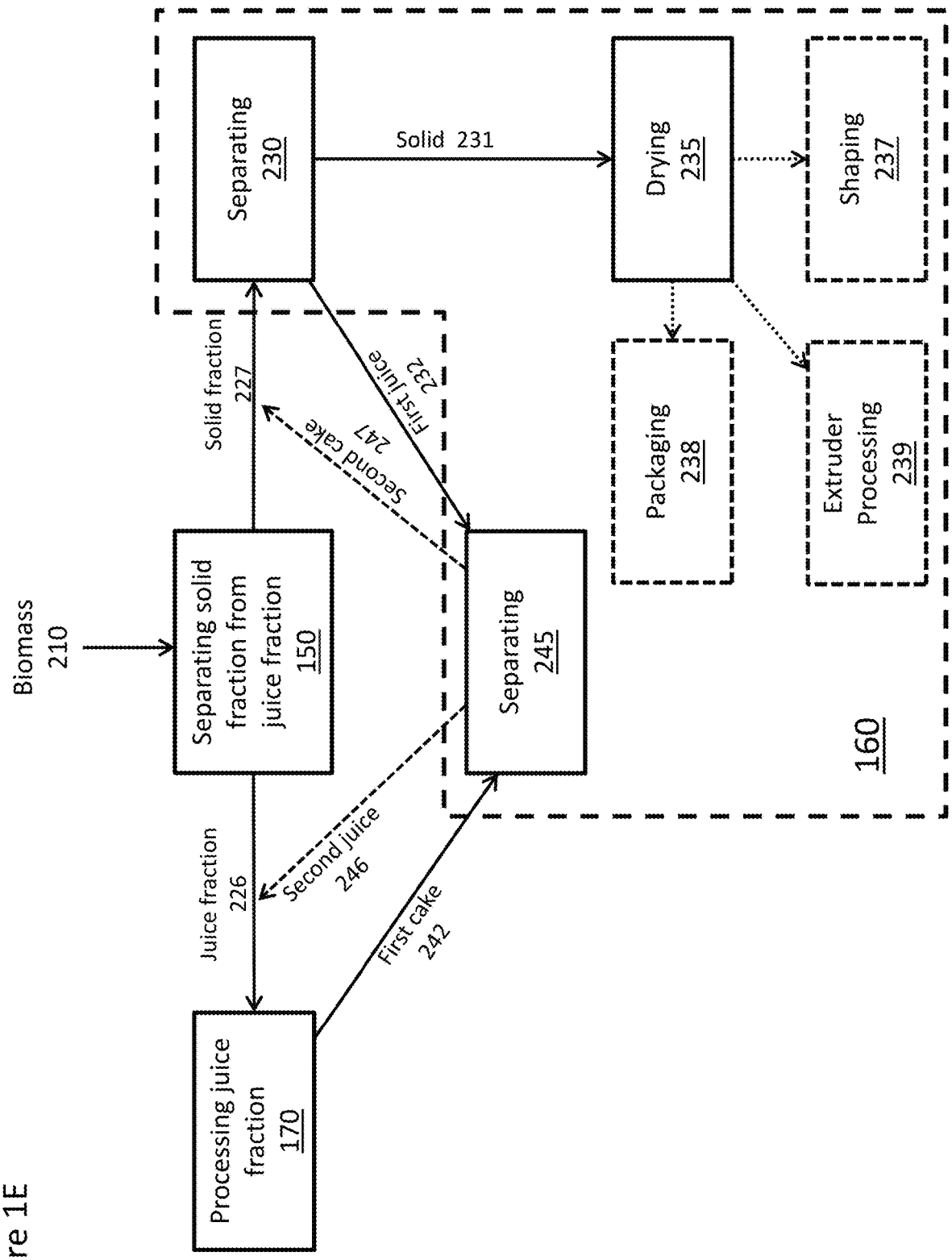
FIG. 1E is a schematic diagram illustrating the separation of a solid fraction from a juice fraction and processing the solid fraction for the production of carbohydrate-rich products according to a specific example embodiment of the disclosure.

FIG. 1E is a schematic diagram illustrating the separation of a solid fraction from a juice fraction and processing the solid fraction for the production of carbohydrate-rich products according to a specific example embodiment of the disclosure;

Separating a Biomass

As shown in FIG. 1E, a biomass 210 may be separated 150 to generate a juice fraction 226 and a solid fraction 227. In some embodiments, a biomass (e.g., *Lemna*) 210 to be separated 150 may be washed, unwashed, lysed, unlysed, or any combination thereof. A juice fraction 226 may include a protein rich liquid and/or at least some solid particles (e.g., carbohydrates, fiber).

Separating 150 a biomass 210, which may have been previously washed and/or lysed, may involve pressing (e.g., belt press), centrifugation, filtration, pressurized filtration, or any combination thereof. Interchangeable unit operations for separating 150 a biomass (e.g., harvested microcrop), washed biomass, and/or lysed biomass include, for example, a decanter centrifuge, a belt press, a fan press, a rotary press, a screw press, a filter press, a finisher press, or any combination thereof.

Separating 150 may be performed at temperatures below room temperature (e.g., 12° C.), for example, to decrease proteolytic activity. In some embodiments, separating may be performed at a temperature below about 40° C., below about 30° C., or below about 20° C., or below about 15° C., or below about 10° C., or below about 15° C., or below about 10° C., or below about 5° C., or below about 2° C., or below about 1° C., or below about 0° C. Separating 225 may be performed at any desired temperature, for example, at a temperature between about 0° C. and about 10° C., or between about 5° C. and about 15° C., or between about 10° C. and about 20° C., or between about 15° C. and about 25° C., or between about 20° C. and about 30° C., or between about 25° C. and about 35° C., or between about 30° C. and about 40° C.

Separating a Solid Fraction

As shown in FIG. 1E, a solid fraction 227 may be further separated 230 to extract additional juice, forming a first juice 232 and a solid 231. In some embodiments, a first juice 232 may include a protein rich liquid and/or at least some solid particles (e.g., carbohydrates, fiber).

Separating a solid fraction 227 to form a first juice 232 and a solid 231 may involve pressing (e.g., belt press), centrifugation, filtration, pressurized filtration, or any combination thereof. Interchangeable unit operations for separating a solid fraction include, for example, a decanter centrifuge, a belt press, a fan press, a rotary press, a screw press, a filter press, a finisher press, or any combination thereof.

In some embodiments, as shown in FIG. 1E for example, other solid fractions (e.g., a first cake 242, a second cake 247) which are collected at other stages in a process (e.g., processing of a juice fraction yields a first cake) may be combined with a solid 231 to form a solid mixture and the solid mixture may be further processed (e.g., by drying 235 and/or shaping 237).

In some embodiments, a moisture content of a solid 231 and/or solid mixture is less than about 90%, or less than about 80%, or less than about 70%, or less than about 60%, or less than about 50%, or less than about 40%, or less than about 30%, or less than about 20%, or less than about 10% by weight.

Recycling Solid Material when Processing Juice Faction

As shown in FIG. 1E, when a juice fraction 226 is processed 170, a first cake 242 may be generated, where the first cake 242 may be a solid material comprising carbohydrates and/or chlorophyll that were not initially separated (e.g., at the action 150) to be part of a solid fraction 227. That is, a first cake 242 may be formed from at least some of the solids remaining in a juice fraction 226. In some embodiments, a first cake 242 and a first juice 232 may be combined and further separated to form a second juice 246 and a second cake 247. According to some embodiments, a first cake 242 and a first juice 232 may be independently subjected to further separation. Separating a first cake 242, a first juice 232, or any combination thereof may involve centrifugation, filtration, pressurized filtration, or any combination thereof, in some embodiments. Several different interchangeable unit operations may be used to separate including, for example, a high-speed disc stack centrifuge, a circular vibratory separator, a linear/inclined motion shaker, a decanter centrifuge, a filter press, pressurized filtration mechanisms, microfiltration, vacuum filtration, or any combination thereof.

Separating may be performed, according to some embodiments, at temperatures below room temperature, for example, to decrease proteolytic activity. In some embodiments separating may be performed at a temperature below about 40° C., or below about 30° C., or below about 20° C., or below about 15° C., or below about 10° C., or below about 15° C., or below about 10° C., or below about 5° C., or below about 2° C., or below about 1° C., or below about 0° C. Separating may be performed at a temperature between about 0° C. and about 10° C., or between about 5° C. and about 15° C., or between about 10° C. and about 20° C., or between about 15° C. and about 25° C., or between about 20° C. and about 30° C., or between about 25° C. and about 35° C., or between about 30° C. and about 40° C., in some embodiments.

As shown in FIG. 1E, a second cake 247 may be combined with a solid 231 to form a solid mixture, in some embodiments, prior to further processing.

Processing a Solid and/or Solid Mixture

A solid 231 and/or solid mixture may be further processed to generate one or more absorptive solids, according to some embodiments. As described previously, a solid mixture may include one or more of a solid 231, a first cake 242, a second cake 247, or any combination thereof that remain after one or more separation processes 150/230/245. An absorptive solids may be suitable for direct use as absorptive products (e.g. animal beddings or in other clean-up applications). Absorbent solids also be suitable as a fuel feedstock or a carbohydrate-rich meal suitable as a human or animal feed supplement (e.g., *Lemna* meal).

In some embodiments, a solid 231 and/or solid mixture may be processed to generate an absorptive solid. According to some embodiments, processing a solid 231 and/or solid mixture may involve drying 235 and/or shaping 237 (e.g., granulation or pelletization).

A process for generating an absorptive solid may be varied depending upon the specific characteristics desired, including, for example, moisture content, particle size, protein content, fat content, fiber content, ash content, chlorophyll content, shelf-life, pellet or granule size and shape, texture, or any combination thereof.

In some embodiments, a solid 231 and/or a solid mixture may be subjected to a drying procedure 235 by a drying unit to reduce a moisture content of a resulting absorptive solid. A drying procedure 235, in some embodiments, may be performed in conjunction with, prior to, or following other processing of a solid 231 and/or a solid mixture, such that an end product is a absorptive solid with a reduced moisture content. A drying procedure 235 may be performed, in some embodiments, using a dryer mechanism including, for example, a spray dryer, double drum dryer, flash dryer, evaporator, or any combination thereof.

In some embodiments, after a drying procedure 235, a solid and/or a solid mixture may be further processed to form an absorptive solid which may be used in a powdered form directly as an absorptive product (e.g. spill clean-up applications). A dried solid and/or solid mixture, in some embodiments, may be shaped 237 by a shaping unit, which may comprise a pelletization machine, a granulator, or other apparatus for shaping the solid 231 and/or solid mixture into groupings (e.g., pellets or granules) that are suitable or convenient for use in or as an absorptive product (e.g. spill clean-up applications, animal bedding). A shaping procedure 237 may result in multiple pellets, granules, or other types of clusters (e.g., of an absorptive solid) which may have a regular shape (e.g., cylindrical or spherical) that are roughly homogenous (e.g., having similar lengths and cross-sectional diameters if cylindrical or having similar diameters if spherical), according to some embodiments. In some embodiments, a shaping 237 may result in heterogeneous and/or irregularly shaped clusters that make up an absorptive product. According to some embodiments, a solid 231 and/or solid mixture may become a final product (e.g. absorptive powder) simply through a drying procedure 235 (e.g., where it is not desired that an absorptive product be shaped).

In some embodiments, after a drying procedure 235, a solid and/or a solid mixture may be further processed by packaging 238 the solid and/or solid mixture into a porous material that physically contains the solid and/or solid mixture while simultaneously allowing external liquid to freely saturate the solid and/or solid mixture. In some embodiments, a packaged solid and/or solid mixture may resemble a large tea bag. In other embodiments, a packaged solid and/or solid mixture may resemble several small tea bags. In some embodiments, a porous packaging may comprise paper, or cotton, or other porous material. In other embodiments, a porous packaging may comprise any combination of paper, cotton, or other porous or biodegradable material.

Characteristics of an Absorptive Solid and/or an Absorptive Product

An absorption coefficient (as measured in liters (L) of liquid absorbed per kilogram (kg) of an absorptive solid) for an absorptive solid (e.g., absorptive pellet, absorptive exudate) may be ≥about 1.48 L/kg, or ≥about 1.4 L/kg, or ≥about 1.3 L/kg, or ≥about 1.2 L/kg, or ≥about 1.1 L/kg, or ≥about 1.0 L/kg, or ≥about 0.9 L/kg, or ≥about 0.8 L/kg, or ≥about 0.7 L/kg, or ≥about 0.6 L/kg, or ≥about 0.5 L/kg, or ≥about 0.4 L/kg, or ≥about 0.3 L/kg, or ≥about 0.2 L/kg, or ≥about 0.1 L/kg in volume of liquid per unit mass of the absorptive solid. According to some embodiments, an absorption coefficient for an absorptive solid (e.g., absorptive powder) may be ≥about 10.0 L/kg, or ≥about 9.0 L/kg, or below about 8.0 L/kg, or ≥about 7.0 L/kg, or ≥about 6.0 L/kg, or below ≥5.0 L/kg, or ≥about 4.0 L/kg, or ≥about 3.0 L/kg, or ≥about 2.0 L/kg, or ≥about 1.0 L/kg, in volume of liquid per unit mass of absorptive product.

A moisture content of an absorptive solid (e.g., absorptive powder, absorptive pellet, absorptive extrudate) and/or an absorptive product (e.g., animal bedding, animal litter, diaper product) may be below about 90%, or below about 80%, or below about 70%, or below about 60%, or below about 50%, or below about 40%, or below about 30%, or below about 20%, or below about 12%, or below about 10%, or below about 5%, or below about 1% by weight of the respective solid or product, in some embodiments.

An absorptive product 168 or absorptive product 169, in some embodiments, may comprise a carbohydrate from a microcrop (e.g., an photosynthetic aquatic species) and an odor-absorbing amount of chlorophyll, at least some of which may also be from the microcrop. In some embodiments, an odor-absorbing amount may be an amount that reduces the odor perceived by one or more humans, which may or may not be assessed through a rigorous sensory analysis. An odor-absorbing amount, in some embodiments, may refer to an amount that reduces the amount of airborne odor-causing particles detectable by any suitable assay. According to some embodiments, an odor-absorbing amount may comprise a wide range of concentrations. For example, a absorptive solid 168 used to generate an absorptive product 169 may comprise a chlorophyll concentration of at least about 50 mg/kg. In some embodiments, an absorptive product 169 may comprise a chlorophyll concentration of at least about 30 mg/kg, or at least about 40 mg/kg, or at least about 50 mg/kg, at least about 60 mg/kg, or at least about 70 mg/kg, or at least about 80 mg/kg, or at least about 90 mg/kg, or at least about 100 mg/kg, or at least about 125 mg/kg, or at least about 150 mg/kg, or at least about 175 mg/kg, or at least about 200 mg/kg, or at least about 225 mg/kg, or at least about 250 mg/kg, or at least about 275 mg/kg, or at least about 300 mg/kg, or at least about 325 mg/kg. In some embodiments, a chlorophyll concentration of a carbohydrate-rich solid may be about 150 mg/kg. Other suitable chlorophyll concentrations may be appropriate for absorbing odor. A chlorophyll concentration of an photosynthetic aquatic species used to derive an absorptive product 169 may also vary. For example, dried *Lemna* may have a chlorophyll concentration of about 850 mg/kg.

Table 1 summarizes the contents of exemplary absorptive solid that may be used to generate an absorptive product. An absorptive product (e.g., animal litter, animal bedding, diaper product) may have the same or similar composition.

TABLE 1

Example Contents of Absorptive Solid and/or Absorptive Product

| | Product A | Product B | Product C |
|---|---|---|---|
| % Solids | ≥~90 | ≥~88 to ~92 | ≥95 |
| % Moisture | ≤~10 | ≤~8 to ~12 | ≤5 |
| % Protein | ≤~20 | from ~10 to ~20 | ≥15-20 |
| % Fat | from ~5 to ~10 | from ~5 to ~20 | ≤5-10 |
| % Ash | ≤~15 | from ~1 to ~20 | ≤5-10 |
| % Carbohydrate | ≥~50 | from ~60 to ~90 | ≥65-70 |
| % Fiber | ≥~50 | ≥~40 | ≥~40 to ~60 |
| Energy (MJ/kg) | ≥~10 | ≥~10 | ≥10 |
| Chlorophyll (mg/kg) | ≥~50 | ~150 | from ~100 to ~300 |

The products shown in Table 1 are for exemplary purposes only, and other compositions may be used to form the absorptive solid that may be used for making an absorbent material. In some embodiments, if a moisture content of an absorptive product undesirably increases during a shaping process (e.g., due to a steam-based pelletization process), this can be compensated by increasing the intensity of a drying process (e.g., increased temperature; increased time of drying; adding an extra drying stage before pelletization).

Clay-based products (e.g., litters) are derived from soil and generally contain silica, which can have harmful respiratory effects. In accordance with the present disclosure, an absorptive product (e.g., animal bedding, diaper product) may be clay-free and may instead be derived from one or more photosynthetic aquatic species that are not grown in soil. Thus, the disclosed absorptive products may not have substantial amounts of silica and may have improved performance and usability for both pet- or human-based applications, and especially for those with weak respiratory capabilities.

Figure 2:
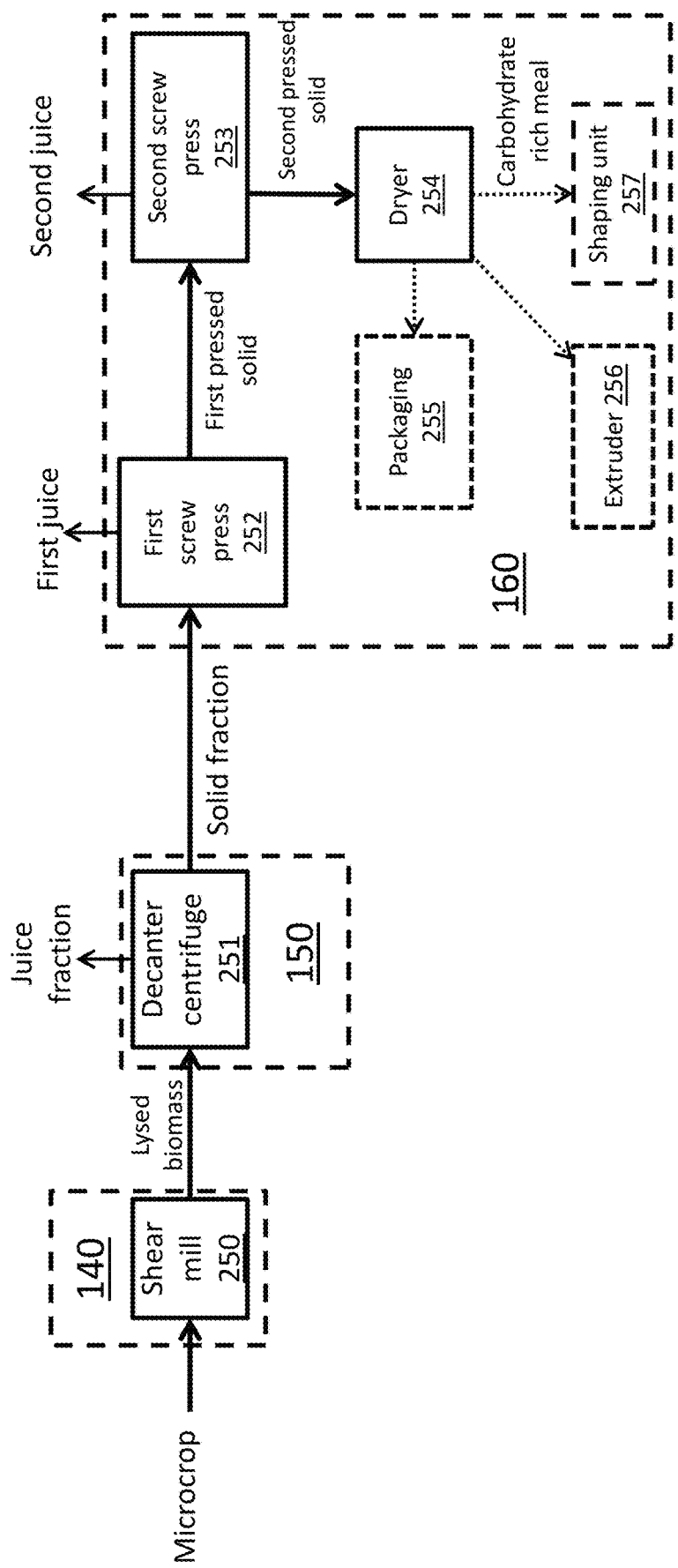
FIG. 2 is a schematic diagram of a process for generating an animal bedding, according to a specific example embodiment of the disclosure.

FIG. 2 is a schematic diagram of a process for generating an absorptive product, according to a specific example embodiment of the disclosure. A microcrop, such as a collection of fronds of fresh *Lemna*, may be conveyed to a shear mill 250 where the fronds may be lysed 140, exposing internal cellular contents and forming a lysed biomass. A lysed biomass may be separated 150 by conveying it to a decanter centrifuge 251, in which the lysed biomass is centrifuged to generate a solid fraction and a juice fraction. In some embodiments, a decanter centrifuge may be replaced or supplemented by a vibratory separator. A solid fraction may be processed 160 by conveying it to a first screw press 252 for further separation into a first pressed solid and a first juice, according to some embodiments.

In some embodiments, a second screw press 253 may further separate solids and liquids, generating a second juice and a second pressed solid, which may have a higher concentration of solid material (e.g., carbohydrates) and lower moisture content than a first pressed solid that is output from a first screw press 252. A second pressed solid ejected from a second screw press may be collected and dried using a dryer 254 (e.g., a spin flash dryer) to generate an absorptive solid that retains at least some of the chlorophyll from a microcrop.

An absorptive product may be produced by packaging 255 a absorptive solid, in a powder form, in a porous material that physically contains the powder while simultaneously allowing external water to freely saturate the powder. In some embodiments, a packaged absorptive product resembles a large tea bag. In other embodiments, a packaged material resembles several small tea bags. A porous material may comprise paper, cotton, any other porous material, or any combination thereof.

Alternatively, an extruder 256 may be used to process an absorptive solid. In some embodiments, an extruder 256 may combine heat, pressure and water inside the extruder 256 with expansion at an output die to induce texture and porosity into a absorptive solid, thereby increasing absorption capacity to greater than a factor of 1.48. In some embodiments, an extrusion process and a drying process may be performed concurrently or subsequently (e.g., first extrude then dry; first dry then extrude).

Alternatively, a solid fraction may be processed using a shaping unit to produce absorptive product. In some embodiments, a shaping unit 257 may comprise a pelletizing unit that pelletizes an absorptive powder or separated solid or absorptive solid. Due to the unique chemical properties of some microcrops, such as *Lemna*, the pelletizing unit may not require heat in some embodiments. This allows for a pelletizing process to begin without waiting for a pelletizing unit to heat up, which is beneficial in embodiments where the pelletizing unit is not operating continuously.

In some embodiments, a shaping unit may be integrated with a dryer, such that an output of the combined drying and shaping unit is a final absorptive product (e.g., animal bedding, spill clean-up). In embodiments where a final product does not need to be shaped (e.g. packaging or extrusion), a shaping unit may not be employed.

A juice fraction from a centrifuge and a first and a second juice from a first and a second screw press, respectively, may be combined to be processed separately from a solid fraction and an absorptive solid (e.g., to form a protein concentrate). While three separation apparatuses and a dryer are described, more, fewer, or different components may be used to generate an absorptive solid and separate a juice fraction and juices. For example, a vibratory separator may be used to separate a solid fraction from a juice fraction and/or to further decrease the moisture content of a solid fraction.

Figure 3:
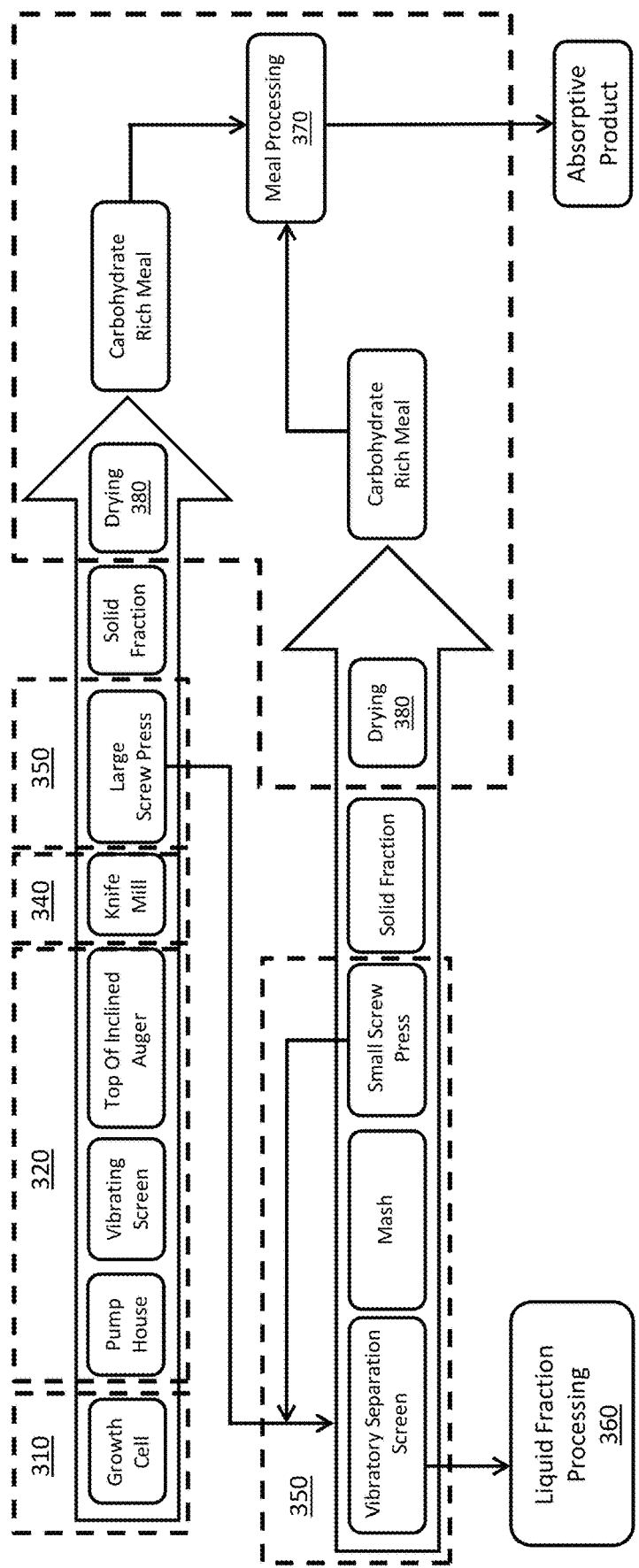
FIG. 3 is a schematic diagram of a process for generating an animal bedding, according to a specific example embodiment of the disclosure.

FIG. 3 is a schematic diagram of a process for generating an absorptive product according to a specific example embodiment of the disclosure. The process may begin by growing 310 a microcrop (e.g., a species of *Lemna*, photosynthetic aquatic species) in a growth cell, which may be within a bioreactor system. A microcrop may be automatically or manually harvested and then transported through a series of automated processes 320 (e.g., a pump hose, a vibrating screen, and an inclined augur) to a lysing unit 340. As shown in the embodiment of FIG. 3, a lysing unit 340 may be a knife mill, which uses a mechanical process to lyse a harvested microcrop, generating a lysed biomass. In other embodiments, different or additional lysing units may be used, as will be described further below.

As shown in FIG. 3, a plurality of separation units 350, such as screw presses and separation screens may be used to separate a solid fraction of a lysed biomass from a juice fraction of the lysed biomass. A solid fraction may, when dried, result in one or more intermediate products such as an absorptive solid. A juice fraction may be separately processed 360, in some embodiments.

Some separation units 350 may work in parallel and with increasing levels of precision to increase yield of intermediate products derived from a microcrop (e.g., absorptive solids) as well as any resulting final products (e.g., absorptive products). For example, a small screw press in combination with a vibratory separation screen may operate on a mixture of a liquid and solid output from a large screw press to generate a solid fraction, which may be dried to generate additional absorptive solid. An absorptive solid from one or more separation units 350 may optionally be combined and processed 370 to form an absorptive product. In some embodiments, a processing 370 unit may also be integrally combined with the one or more drying units 380. In embodiments where a pelletized, granulated, or otherwise shaped absorptive solid or absorptive product is not desired, a shaping unit may be bypassed or replaced by another solid fraction processing unit that produces an absorptive solid or absorptive product of the desired form (e.g., a free fine or course powder, packaged fine or course powder).

According to some embodiments, a juice fraction from a lysed biomass may also be processed 360 to generate one or more products such as a dried protein product and a liquor.

Figure 4:
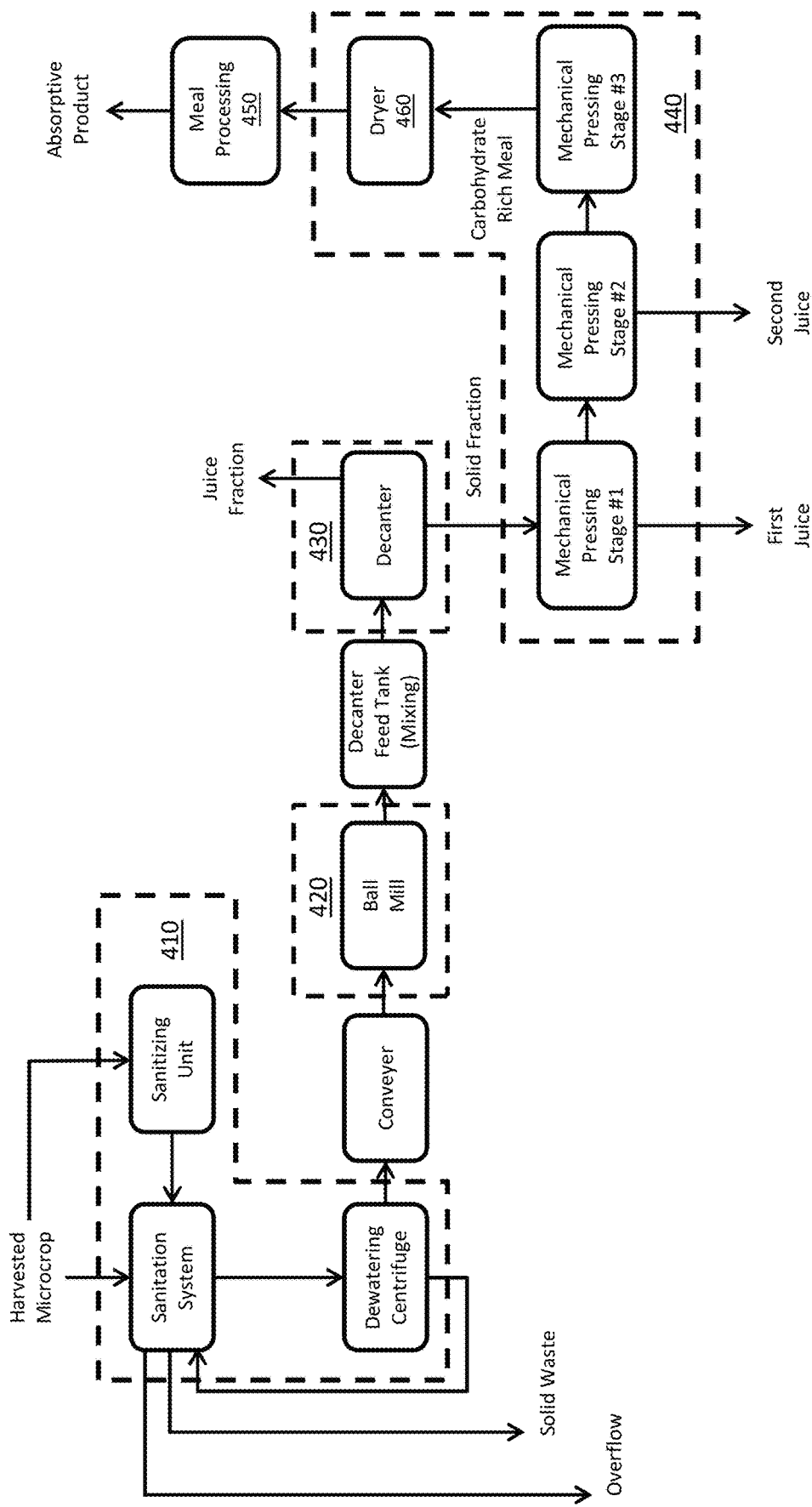
FIG. 4 is a schematic diagram of a process for generating an animal bedding, according to a specific example embodiment of the disclosure.

FIG. 4 is a schematic diagram of a process for generating an absorptive product, according to a specific example embodiment of the disclosure. A harvested microcrop, such as a species of *Lemna* or another photosynthetic aquatic species, may be sanitized 410 by conveying to a sanitation system that washes or otherwise cleans a harvested microcrop. An overflow and/or solid waste resulting from washing a harvested microcrop may be discarded or recycled, according to some embodiments. In some embodiments, a washed microcrop may be conveyed to a dewatering centrifuge, which separates at least some of a wash water from the washed microcrop. A separated water, in some embodiments, is recycled back to a sanitation system. As shown in FIG. 4, a washed microcrop may be conveyed to a lysing unit 420 (e.g. a ball mill) where it may be lysed forming a lysed biomass.

In the embodiment of FIG. 4, a lysed biomass may be separated into a solid fraction and a juice fraction through a decanter 430. A solid fraction may be further processed 440 by three mechanical pressing stages and a dryer stage. In general, a greater or lesser number of solid processing stages may be implemented, depending on system requirements such as cost, purity, and available technology. In some embodiments, a lysed biomass passes through each of a separation and a solid processing stage such that a solid and/or a juice are output at each stage. Some stages (e.g., a third mechanical pressing stage and a dryer stage) may produce limited amounts of liquid or juice that may make recovery of an extracted juice inefficient from those stages.

In some embodiments, an absorptive solid may be further processed 450 to produce an absorptive product. According to some embodiments, a resulting solid, which may be an absorptive solid, may be processed 450 by packaging the resulting solid, in a powdered form, into a porous material to generate an absorptive product. According to other embodiments, an extruder may be used to process 450 the resulting solid, combining heat, pressure and water inside the extruder with expansion at the output die to induce texture and porosity into an absorptive product. According to some embodiments, a resulting solid, which may be an absorptive solid (e.g. absorptive powder), may be processed 450 by a pelletizing unit to generate an absorptive product. In some embodiments, a pelletizing unit may not substantially heat or change a composition of an absorptive solid, and instead merely forms an absorptive solid into pellets that make up an absorptive product. A pelletizing unit, in some embodiments, may apply heat and/or a binding agent to form pellets and may thus alter a chemical composition of an absorptive product (e.g., by lowering the moisture content). Steam may be used to produce a firmer pellet if desired, which may also increase a moisture content.

A pelletizing unit may be a pellet mill that uses a flat die, a ring die, or any other type of mechanism to extrude cylindrical portions of modified or unmodified carbohydrate-rich meal, according to some embodiments. One or more blades may be used to cut a cylindrical portions as they are extruded, thereby forming pellets. In some embodiments, pellets may have a width of about 4 millimeters (mm) and a length in a range of about 8 mm to about 10 mm. However, larger, smaller, or differently proportioned pellets may also be generated depending, e.g., on the intended usage scenarios. These dimensions may be established based on factors of a pelletizing unit, such as die type and cutting frequency. A pelletizing unit may be tunable to vary the dimensions of pellets, or it may be interchanged with a different pelletizing unit. In embodiments where a desired absorptive product is not in pellet form, a pelletizing unit may be bypassed.

Other units may be employed in processing 450 an absorptive solid into an absorptive product having different shapes (e.g., disks, spheres, extruded cylinders) and/or powdered forms. In some embodiments it may be advantageous to process an absorptive solid (e.g. absorptive powder) into granules. Granulation may be accomplished directly in the drying process 460 by using a fluid bed dryer whose parameters are adjusted to deliver a granular output instead of a powder output. In other embodiments, a dried powder may be subject to a granulation process as a separate processing step.

In some embodiments, an extruder may be employed during processing 450 to extrude segments (e.g., pellets, expanded pellets or granules) of an absorptive product having a generally constant cross-section. An extruder may use a flat die, a ring die, or any other type of mechanism to extrude cylindrical portions of modified or unmodified absorptive solid, according to some embodiments. One or more blades may be used to cut cylindrical portions as they are extruded, thereby forming extrudates (e.g. pellets, expanded pellets or granules). In some embodiments, extrudates may have a width of about 4 millimeters (mm) and a length in a range of about 8 mm to about 10 mm. However, larger, smaller, or differently proportioned extrudates may also be generated depending, e.g., on the intended usage scenarios. These dimensions may be established based on factors of an extruder, such as die type and cutting frequency. An extruder may be tunable to vary the dimensions of extrudates, or it may be interchanged with a different extruder. In some embodiments, an extruder may couple heat, pressure and water inside the extruder with expansion at the output die to induce texture and porosity into the absorptive product. In some embodiments the size and cross section of an absorptive product may vary.

In some embodiments, an absorptive solid may be alternatively packaged as a powder in a porous material that physically contains the powder while simultaneously allowing an external liquid to freely saturate the powder. In one embodiment, such a packaging would resemble a large tea bag containing the absorptive powder. In another embodiment, such packaging would resemble several small tea bags containing the absorptive powder. In some embodiments, an absorptive powder may have an absorption coefficient of up to 10 L/kg.

Figure 5B:
FIG. 5B illustrates the performance of a wood-based animal litter when exposed to liquid.
Figure 5C:
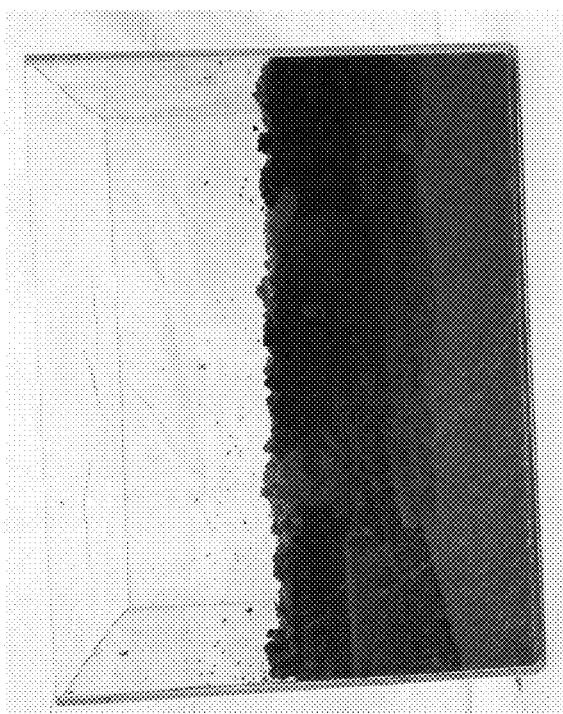
FIG. 5C illustrates the performance of a specific example embodiment of a *Lemna*-based animal litter when exposed to liquid.
Figure 5A:
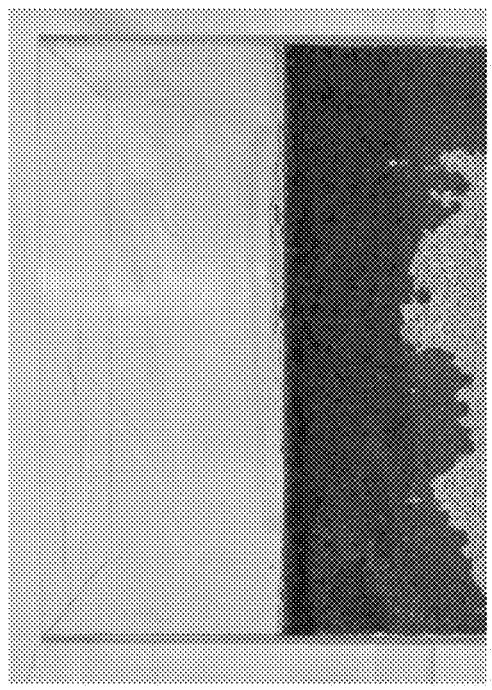
FIG. 5A illustrates the performance of a clay-based animal litter when exposed to liquid.

FIGS. 5A-5C are pictures illustrating tests to determine performance of an absorptive product formed, in accordance with the disclosed principles, from a particular photosynthetic aquatic species, Lemna, relative to other types of absorptive products (i.e. cat litters). Specifically, moisture absorption properties of a Lemna-based litter were compared to those of a clay-based litter and a pine-based cat litter. In each test, a litter was placed inside of a glass container and liquid was gradually dropped into the container, in 100 milliliter (ml) increments, until a failure criterion was met. A first failure criterion was when a litter was fully saturated (e.g., such that a layer of liquid formed and remained on the surface of the litter), and a second failure criterion was when a glass container overflowed with litter or liquid. It may be noted that a fixed size of the container was chosen to reflect practical considerations. That is, as the size of a litter box increases, it becomes increasingly difficult for a user to replace the litter within it or to clean the litter box itself. Accordingly, litter boxes cannot arbitrarily be increased in size to contain additional litter. These failure criterion were based upon the practical conditions at (or ideally before) which time the litter would need to be replaced by a user (e.g., pet owner). Accordingly, it was a goal to absorb the most liquid before a failure criterion was met. The liquid was dyed to more clearly show its diffusion into each litter.

FIG. 5A specifically illustrates a performance of a clay-based animal litter when exposed to liquid. After 800 ml of a liquid was added, a clay-based animal litter was fully saturated and remained in the saturated state for at least 30 minutes. Accordingly, the first failure criterion was met. While there were portions near the bottom of the litter that remained dry, they could not be used because liquid could not pass through the saturated top portions.

FIG. 5B illustrates a performance of a wood-based animal litter when exposed to liquid. The pine pellets dissolved into sawdust upon their exposure to liquid, where the sawdust consumed significantly more volume than the pine pellets. After 2300 ml was added, the expansion of the litter caused it to begin spilling over the sides of the container, and thus the second failure criterion was met.

FIG. 5C illustrates a performance of a *Lemna*-based animal litter formed in accordance with the present disclosure when the litter was exposed to liquid.

This litter was able to absorb 2600 ml of liquid before becoming saturated and the first failure criterion was met. While it was noticed that *Lemna*-based pellets did expand upon being exposed to liquid, the degree of expansion was less. Furthermore, the *Lemna*-based pellets were better able to maintain their structure and did not break apart to the same extent as the pine-based pellets. These properties beneficially simplify a user's task when changing a litter box.

Table 2 below summarizes test conditions and results illustrated in FIGS. 5A, 5B, and 5C and shows that a product based on an photosynthetic aquatic species (*Lemna*) was able to absorb the most liquid and had the highest absorption coefficient (e.g., as measured in liters (l) of liquid absorbed per kilogram (kg) of litter before a failure criterion was met). It was a surprising discovery that a litter based upon material from an aquatic plant outperformed the other types of litter in terms of liquid absorption.

TABLE 2

Absorption Performance Comparison between Litters

|  | Clay-based product | Pine-based product | Lemna-based product |
|---|---|---|---|
| Weight of litter (kg) | 1.168 | 1.610 | 1.761 |
| Total liquid absorbed before saturation (ml) | 800 | 2300 | 2600 |
| Absorption coefficient (l/kg) | 0.68 | 1.43 | 1.48 |

Figure 6:
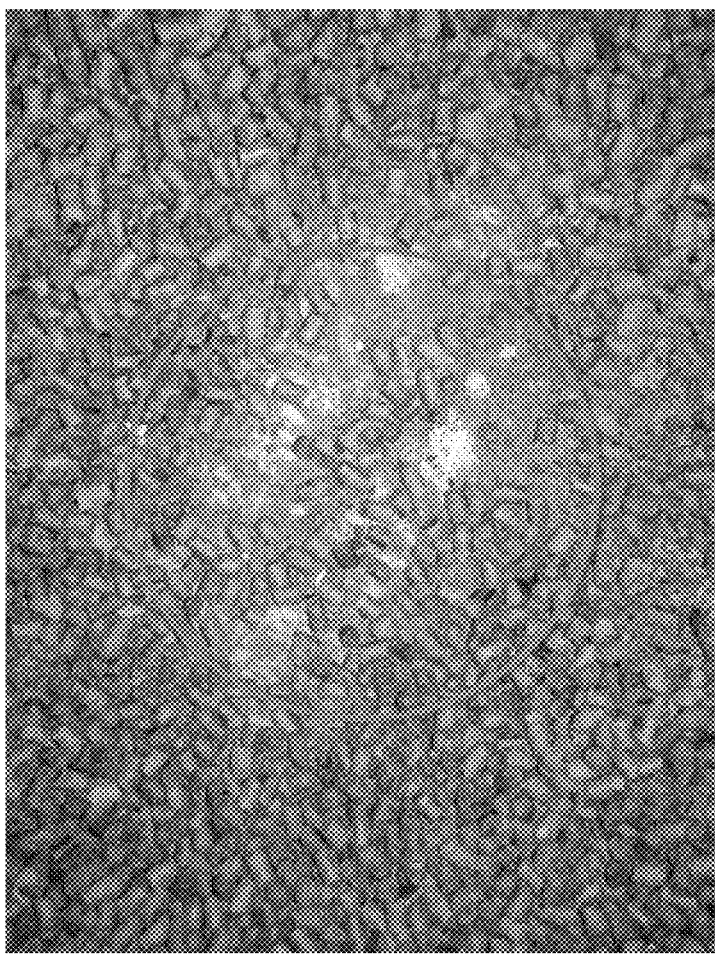
FIG. 6 illustrates aspects of a specific example embodiment of a *Lemna*-based animal litter.

FIG. 6 illustrates aspects of a specific example embodiment of a *Lemna*-based animal litter. The animal litter of FIG. 6 was produced using *Lemna*. It was found such pellets were able to dry very quickly when exposed to cat urine and also rapidly covered the odor as a result. It was further determined that the pellets changed color upon being used (e.g., by contacting with animal waste). As shown within the annotated circle, the *Lemna*-based pellets changed from a dark green color to a noticeably different light brown color upon being exposed to urine and then drying. This color-changing property beneficially improves detection and simplifies the clean-up process. For example, an owner may use the color as an indication to change the litter, and may also selectively remove and replace expired pellets with fresh pellets.

Figure 7A:
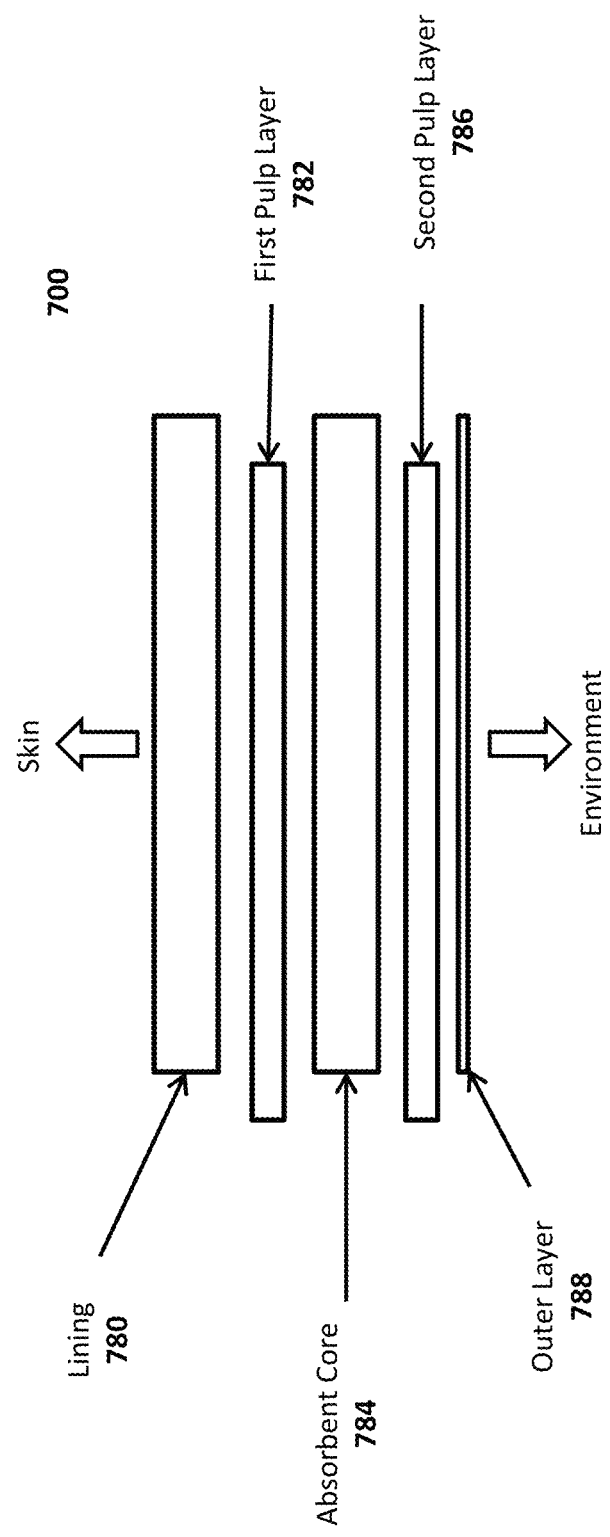
FIG. 7A illustrates a cross section of a specific example embodiment of a diaper product.

FIG. 7A illustrates a cross-sectional view of a specific example embodiment of a diaper product which comprises a microcrop-derived absorbent core. In some embodiments, a diaper product 700 may comprise a lining 780, a first pulp layer 782, an absorbent core 784, a second pulp layer 786, and an outer layer 788. In some embodiments, the lining 780 may be designed to be in direct contact with skin and may therefore comprise a fleece-like material layer which allows skin to breathe. In other embodiments, the lining 780 comprises a material other than fleece-like material which allows skin to breathe. Persons skilled in the art may make various changes in the composition of the lining 780 without departing from the scope of the instant disclosure.

In some embodiments, a diaper product 700 may further comprise a first pulp layer 782 which may lie superficially to a lining 780. According to some embodiments, a first pulp layer 782 may comprise a combination of cotton wool and pulp, which may be weaved together to form a single material prior to the assembly of a diaper product. In some embodiments a first pulp layer may comprise a combination of cotton wool and another material, weaved together to form a single material prior to the assembly of a diaper product. Persons skilled in the art may make various changes in the composition of a first pulp layer 782 without departing from the scope of the instant disclosure.

In some embodiments, a diaper product 700 may further comprise an absorbent core 784, which may lie superficially to a first pulp layer 782. An absorbent core 784 may comprise an absorptive solid. In some embodiments, an absorbent core may comprise an absorbent powder, an absorbent pellet, an absorbent extrudate, or any combination thereof. An absorptive product may be incorporated into an absorbent core 784 as an absorbent powder in a porous material that physically contains the powder while simultaneously allowing external water to freely saturate the powder. In some embodiments, the packaged absorptive solid may resemble a large tea bag. A package containing an absorptive solid may be quilted to ensure consistent distribution of the powdered absorptive solid across the entire area of a package. In other embodiments, a packaged, powder absorptive solid would resemble many small tea bags. In some embodiments, an absorbent core 784 may comprise an absorbent pellet, an absorbent extrudate, or a combination thereof packaged in a porous material that physically contains the pellets and/or extrudates. In some embodiments, an absorbent core 784 may comprise an absorptive solid and another absorptive material (e.g. cotton, pulp). According to some embodiments, an absorbent core 484 may further comprise a chlorophyll additive that may act as a deodorizer. In some embodiments, an absorbent core 484 may further comprise a sodium polyacrylate. Persons skilled in the art may make various changes in the composition of an absorbent core 784 without departing from the scope of the instant disclosure.

In some embodiments, a diaper product 700 may further comprise a second pulp layer 786 which may lie superficially to an absorbent core 784. According to some embodiments, a second pulp layer 782 may comprise a combination of cotton wool and pulp, which may be weaved together to form a single material prior to the assembly of a diaper product. In some embodiments a second pulp layer may comprise a combination of cotton wool and another material, weaved together to form a single material prior to the assembly of a diaper product. A second pulp layer 786 may have the same or a different composition from a first pulp layer 782. Persons skilled in the art may make various changes in the composition of a second pulp layer 786 without departing from the scope of the instant disclosure.

In some embodiments, a diaper product 700 may further comprise an outer layer 788 which may lie superficially to a second pulp layer 786. An outer layer 788 may comprise a material that has been made waterproof in order to prevent leakage of liquid onto a superficial side of an outer layer 788. An outer layer 788 may comprise a petroleum-based plastic material or another material that has been treated with a petroleum-based plastic on its superficial side. Additionally, an outer layer 788 may comprise polylactic acid or another plant-based plastic or a combination of polylacetic acid and another material or a combination of another plant-based plastic and another material. Persons skilled in the art may make various changes in the composition of an outer layer 788 without departing from the scope of the instant disclosure.

Figure 7B:
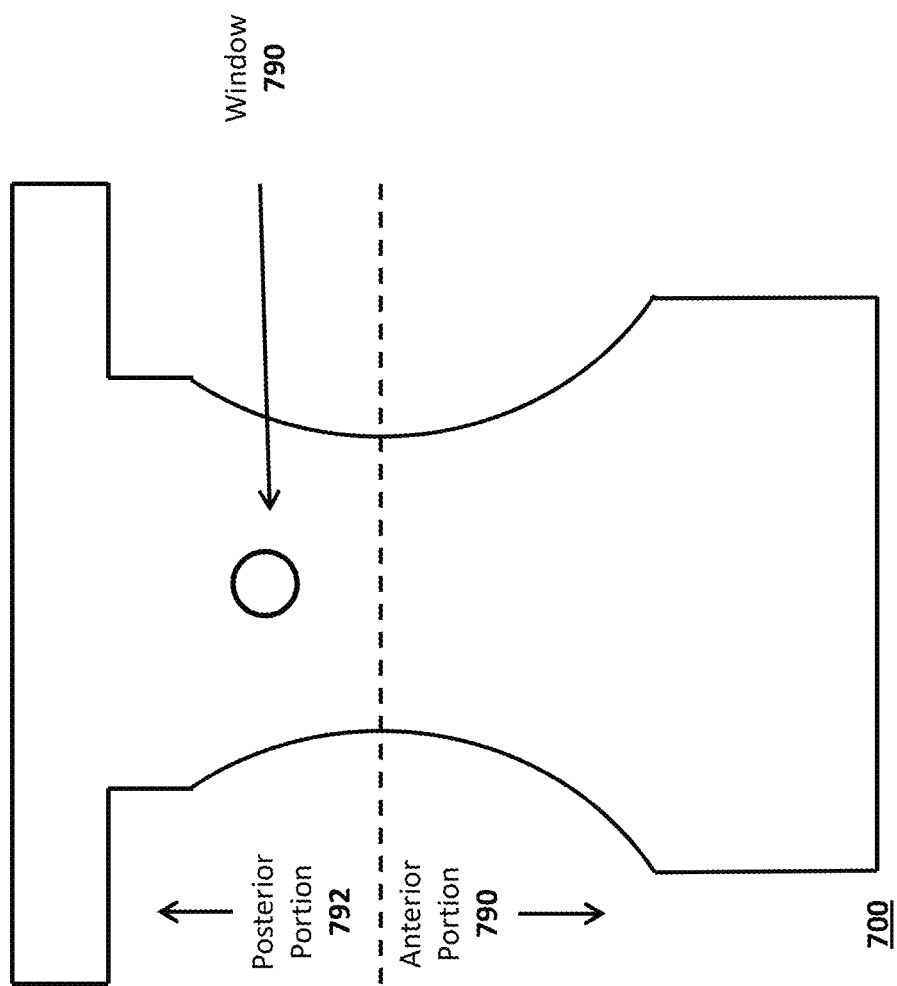
FIG. 7B illustrates a specific example embodiment of a diaper product.

In some embodiments, a diaper product 788 may further comprise an observational means to determine when a diaper product has reached a certain absorbent capacity. FIG. 7B illustrates a specific embodiment of a diaper product 700 wherein an observational means is a transparent window 790, through which a color change may be observed. In some embodiments, a window 790 may be translucent. A window 790 or other observational means may be located on a superficial face of the anterior portion 790 of a diaper product in some embodiments. As shown in FIG. 7B, according to some embodiments, a window 790 or other observational means may also be located on a superficial face of a posterior portion 792 of a diaper product. A window 790 or other observational means may be constructed of any transparent or translucent material as deemed appropriate by one who is skilled in the art. A window 750 or other observational means may be used to view an absorbent core 730 to determine when an absorptive solid or absorptive product has reached a particular percentage of saturation. In some embodiments, an absorbent core 730 may undergo a color change at a particular percentage of saturation. As shown in FIG. 3, a Lemna-based absorptive product changes from a dark green color to a noticeably different light brown color upon being exposed to urine and then drying. This color-changing property beneficially improves detection and simplifies the clean-up process. Persons skilled in the art may make various changes in the shape, size, number, composition and/or arrangement of parts without departing from the scope of the instant disclosure.

When created using some embodiments of the systems and methods disclosed herein, an absorptive product may provide a variety of other benefits such as being naturally non-clumping and hypoallergenic. With respect to an animal bedding embodiment, further experimental evidence suggested that these properties may greatly increase certain animals' affinity to such a bedding, and especially those with increased dermal sensitivity. As such, it may be relatively easy for pet owners to transition their pets from using different beddings to those in accordance with the disclosure. In some embodiments, microcrop-based beddings may be fully biodegradable. Accordingly, such products may be incorporated as organic fertilizers or composts after use, thereby further increasing the total utility they may provide.

Embodiments of the disclosure provide systems of producing an absorptive product from microcrop (e.g., photosynthetic aquatic species such as Lemna). As described herein, such systems can include, for example: a lysing unit for lysing a microcrop to generate a lysed microcrop; a separating unit for separating the lysed microcrop into a solid fraction and a juice fraction; and a unit for processing the solid fraction (e.g., pelletizing unit). Summarized in Table 3 are apparatuses that may be included, either individually or in combination, in these units. Manual or automatic processes may be implemented to move material between the different units.

TABLE 3

| | Example Apparatuses and Techniques |
|---|---|
| Lysing unit | Shear mill, Colloid mill, knife mill, hammer mill, grinding mill, puree machine, filter press, sonication, pH adjustment |
| Separating unit | Belt press, decanter centrifuge, fan press, rotary press, screw press, filter press, finisher press, linear/circular vibratory separator, vibrating screen filter, linear/inclined motion shaker, decanter centrifuge, high-speed disc stack centrifuge, microfiltration, ultrafiltration, spray dryer, drum dryer, flash dryer, spin flash dryer, fluid bed dryer |
| Unit for processing solid fraction (e.g., comprising a shaping unit) | Flat die mill, ring die mill, heated pellet compression units, cold pellet compression units, steam-based pellet compression unit, high-shear granulator, twin screen granulator, fluidized bed granulator, dry granulator, spray dryer, drum dryer, flash dryer, spin flash dryer, fluid bed dryer, rotary press, screw press, filter press, finisher press, extruder |

The disclosed microcrop-based products may also be adapted to other applications or usage scenarios.

As will be understood by those skilled in the art who have the benefit of the instant disclosure, other equivalent or alternative compositions, devices, methods, and systems for forming animal bedding can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, the position, number, and type of lysing units, separating units, units for processing solid fractions, and other units may be varied. In some embodiments, some or all of these units may be interchangeable. Interchangeability may allow odor control, liquid absorption, and other features to be custom adjusted (e.g., by varying chlorophyll, carbohydrate, and/or moisture content). In addition, the size of a device and/or system may be scaled up (e.g., to be used for high volume production facilities) or down (e.g., to be used for low volume production facilities) to suit the needs and/or desires of a practitioner. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a composition, device, and/or system of the disclosure. For example, a composition, device, and/or system may be prepared and or used as appropriate for animal and/or human use (e.g., with regard to sanitary, infectivity, safety, toxicity, biometric, and other considerations). As a further example, a pelletizing unit may be bypassed in embodiments where the animal bedding is desired to be in a non-pellet form. Elements, compositions, devices, systems, methods, and method steps not recited may be included or excluded as desired or required.

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value +/−about 10%, depicted value +/−about 50%, depicted value +/−about 100%) and/or a range endpoint. With respect to the former, a value of 50 depicted in an example, table, and/or drawing may form the basis of a range of, for example, about 45 to about 55, about 25 to about 100, and/or about 0 to about 100. Disclosed percentages are weight percentages except where indicated otherwise.

All or a portion of a device and/or system for producing an animal bedding and/or litter may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

The title, abstract, background, and headings are provided in compliance with regulations and/or for the convenience of the reader. They include no admissions as to the scope and content of prior art and no limitations applicable to all disclosed embodiments.

What is claimed is:

1. A diaper product comprising an absorbent layer having at least one package composed of a porous material, the porous material containing an absorptive product comprising:
   an odor-absorbing amount of chlorophyll; and
   a carbohydrate extracted from a photosynthetic aquatic species and comprising:
   (1) at least a portion of the odor-absorbing amount of chlorophyll, and
   (2) at least one of:
      an absorptive powder having an absorptive coefficient that is >9.0 L/kg;
      an absorptive pellet having an absorption coefficient that is >1.44 L/kg; and
      an absorptive extrudate having an absorption coefficient that is >1.44 L/kg.

2. The diaper product of claim 1, wherein the photosynthetic aquatic species is selected from the group consisting of *Lemna, Spirodela, Landoltia, Wolfiella, Salvinia, Wolffia, Azolla, Pistia*, and any combination thereof.

3. The diaper product of claim 1, wherein the absorptive product comprises at least 150 mg/kg of chlorophyll of which the carbohydrate comprises at least 50 mg/kg of chlorophyll.

4. The diaper product of claim 1, wherein the absorptive pellet has an average length in a range of about 8-10 millimeters and an average width of about 4 millimeters.

5. The diaper product of claim 1, wherein at least one of the absorptive powder, the absorptive pellet, and the absorptive extrudate has a moisture content that is less than about 12%, by weight.

6. The diaper product of claim 1, wherein the absorptive pellet has a carbohydrate content that is greater than about 50%, by weight.

7. The diaper product of claim 1, wherein the absorptive pellet has a liquid absorption coefficient greater than or substantially equal to 1.48 liters of liquid per kilogram of pellets.

8. The diaper product of claim 1, wherein the absorptive pellets remain intact and do not clump with each other after being exposed to a liquid.

* * * * *